US010159411B2

(12) United States Patent
Tzvieli et al.

(10) Patent No.: US 10,159,411 B2
(45) Date of Patent: Dec. 25, 2018

(54) DETECTING IRREGULAR PHYSIOLOGICAL RESPONSES DURING EXPOSURE TO SENSITIVE DATA

(71) Applicants:Arie Tzvieli, Berkeley, CA (US); Gil Thieberger, Kiryat Tivon (IL); Ari M Frank, Haifa (IL)

(72) Inventors: Arie Tzvieli, Berkeley, CA (US); Gil Thieberger, Kiryat Tivon (IL); Ari M Frank, Haifa (IL)

(73) Assignee: Facense Ltd., Kiryat Tivon (IL)

( * ) Notice: Subject to any disclaimer, the term of this patent is extended or adjusted under 35 U.S.C. 154(b) by 0 days.

(21) Appl. No.: 15/859,772

(22) Filed: Jan. 2, 2018

(65) Prior Publication Data

US 2018/0116528 A1   May 3, 2018

Related U.S. Application Data

(63) Continuation-in-part of application No. 15/722,434, filed on Oct. 2, 2017, which is a continuation-in-part
(Continued)

(51) Int. Cl.
*A61B 5/01* (2006.01)
*A61B 5/00* (2006.01)
*A61B 5/16* (2006.01)

(52) U.S. Cl.
CPC .............. *A61B 5/01* (2013.01); *A61B 5/0077* (2013.01); *A61B 5/165* (2013.01); *A61B 5/6803* (2013.01); *A61B 5/7264* (2013.01)

(58) Field of Classification Search
CPC .... G02C 11/00; G02C 11/04; G02C 2200/16; G02C 5/14; G02C 7/02; A61B 5/6803;
(Continued)

(56) References Cited

U.S. PATENT DOCUMENTS

| 5,143,086 A | * | 9/1992 | Duret | A61B 5/1127 600/590 |
| 5,664,578 A | | 9/1997 | Boczan | |

(Continued)

FOREIGN PATENT DOCUMENTS

| EP | 2233071 A1 | 9/2013 |
| WO | WO2016025323 | 2/2016 |

OTHER PUBLICATIONS

Alghoul, K., Alharthi, S., Al Osman, H., & El Saddik, A. (2017). Heart Rate Variability extraction from video signals: ICA vs. EVM comparison. IEEE Access, 5, 4711-4719.
(Continued)

*Primary Examiner* — David Porta
*Assistant Examiner* — Faye Boosalis
(74) *Attorney, Agent, or Firm* — Active Knowledge Ltd.

(57) ABSTRACT

A system that detects an irregular physiological response while being exposed to sensitive data includes: a head-mounted display (HMD), an inward-facing head-mounted thermal camera (CAM), and a computer. The HMD exposes sensitive data to the user who wears the HMD. The CAM takes thermal measurements of a region of interest ($TH_{ROI}$) on the user's face while the user is exposed to the sensitive data. And the computer detects, based on certain $TH_{ROI}$ taken while the user was exposed to certain sensitive data, whether the user experienced the irregular physiological response while being exposed to the certain sensitive data.

20 Claims, 13 Drawing Sheets

Related U.S. Application Data of application No. 15/182,592, filed on Jun. 14, 2016, and a continuation-in-part of application No. 15/231,276, filed on Aug. 8, 2016, and a continuation-in-part of application No. 15/284,528, filed on Oct. 3, 2016, now Pat. No. 10,113,913, application No. 15/859,772, which is a continuation-in-part of application No. 15/635,178, filed on Jun. 27, 2017, now Pat. No. 10,136,856, and a continuation-in-part of application No. 15/284,528, filed on Oct. 3, 2016, now Pat. No. 10,113,913, and a continuation-in-part of application No. 15/231,276, filed on Aug. 8, 2016, and a continuation-in-part of application No. 15/182,592, filed on Jun. 14, 2016.

(60) Provisional application No. 62/566,572, filed on Oct. 2, 2017, provisional application No. 62/408,677, filed on Oct. 14, 2016, provisional application No. 62/456,105, filed on Feb. 7, 2017, provisional application No. 62/480,496, filed on Apr. 2, 2017, provisional application No. 62/175,319, filed on Jun. 14, 2015, provisional application No. 62/202,808, filed on Aug. 8, 2015, provisional application No. 62/236,868, filed on Oct. 3, 2015, provisional application No. 62/354,833, filed on Jun. 27, 2016, provisional application No. 62/372,063, filed on Aug. 8, 2016.

(58) Field of Classification Search
CPC ..... A61B 5/015; A61B 5/0878; A61B 5/1118; A61B 5/6801; A61B 5/6847; A61F 9/04; G02B 2027/0138; G02B 27/017
See application file for complete search history.

(56) References Cited

U.S. PATENT DOCUMENTS

| | | | |
|---|---|---|---|
| 6,121,953 A | 9/2000 | Walker | |
| 6,286,958 B1 | 9/2001 | Koest et al. | |
| 6,771,423 B2 | 8/2004 | Geist | |
| 6,837,615 B2 | 1/2005 | Newman | |
| 6,996,256 B2 | 2/2006 | Pavlidis | |
| 7,027,621 B1 | 4/2006 | Prokoski | |
| 7,135,980 B2 | 11/2006 | Moore et al. | |
| 7,138,905 B2 | 11/2006 | Pavlidis et al. | |
| 8,149,273 B2 | 4/2012 | Liu et al. | |
| 8,289,443 B2 | 10/2012 | MacKenzie | |
| 8,334,872 B2 | 12/2012 | Epps et al. | |
| 8,360,986 B2 | 1/2013 | Farag et al. | |
| 8,573,866 B2 | 11/2013 | Bond et al. | |
| 8,585,588 B2 | 11/2013 | Kovarik et al. | |
| 8,723,790 B1 | 5/2014 | Schaefer | |
| 8,768,438 B2 | 7/2014 | Mestha et al. | |
| 8,786,698 B2 | 7/2014 | Chen et al. | |
| 8,855,384 B2 | 10/2014 | Kyal et al. | |
| 8,964,298 B2 | 2/2015 | Haddick et al. | |
| 9,019,174 B2 | 4/2015 | Jerauld | |
| 9,020,185 B2 | 4/2015 | Mestha et al. | |
| 9,194,749 B2 | 11/2015 | Pompei | |
| 9,211,069 B2 | 12/2015 | Larsen et al. | |
| 9,410,854 B2 | 8/2016 | Padiy | |
| 9,569,734 B2 | 2/2017 | Thieberger et al. | |
| 2002/0080094 A1 | 6/2002 | Biocca et al. | |
| 2005/0083248 A1 | 4/2005 | Biocca et al. | |
| 2005/0271117 A1 | 12/2005 | Grassl et al. | |
| 2007/0047768 A1 | 3/2007 | Gordon et al. | |
| 2007/0248238 A1 | 10/2007 | Abreu | |
| 2007/0265507 A1 | 11/2007 | de Lemos | |
| 2008/0260212 A1 | 10/2008 | Moskal et al. | |
| 2009/0221888 A1 | 9/2009 | Wijesiriwardana | |
| 2009/0237564 A1 | 9/2009 | Kikinis et al. | |
| 2010/0191124 A1 | 7/2010 | Prokoski | |
| 2010/0280334 A1 | 11/2010 | Carlson et al. | |
| 2012/0062719 A1 | 3/2012 | Debevec et al. | |
| 2012/0105473 A1 | 5/2012 | Bar-Zeev et al. | |
| 2012/0197093 A1 | 8/2012 | LeBoeuf et al. | |
| 2012/0327194 A1 | 12/2012 | Shiratori et al. | |
| 2013/0124039 A1 | 5/2013 | Abreu | |
| 2013/0215244 A1 | 8/2013 | Mestha et al. | |
| 2013/0241805 A1 | 9/2013 | Gomez | |
| 2013/0257709 A1 | 10/2013 | Raffle et al. | |
| 2014/0180449 A1 | 6/2014 | Sung | |
| 2014/0282911 A1 | 9/2014 | Bare et al. | |
| 2014/0347265 A1 | 11/2014 | Aimone et al. | |
| 2014/0366049 A1 | 12/2014 | Lehtiniemi et al. | |
| 2015/0087924 A1 | 3/2015 | Li et al. | |
| 2015/0148618 A1 | 5/2015 | Sitko et al. | |
| 2015/0157255 A1 | 6/2015 | Nduka | |
| 2015/0297126 A1 | 10/2015 | Atsumori et al. | |
| 2015/0310263 A1 | 10/2015 | Zhang et al. | |
| 2015/0359443 A1 | 12/2015 | Poh | |
| 2016/0015289 A1 | 1/2016 | Simon et al. | |
| 2016/0081622 A1 | 3/2016 | Abreu | |
| 2016/0091877 A1 | 3/2016 | Fullam et al. | |
| 2016/0098592 A1 | 4/2016 | Lee et al. | |
| 2016/0100790 A1 | 4/2016 | Cantu et al. | |
| 2016/0170996 A1 | 6/2016 | Frank et al. | |
| 2016/0216760 A1 | 7/2016 | Trutna et al. | |
| 2016/0224803 A1* | 8/2016 | Frank | G06F 21/6245 |
| 2016/0235324 A1 | 8/2016 | Mershin et al. | |
| 2016/0270656 A1* | 9/2016 | Samec | A61B 3/085 |
| 2016/0342835 A1 | 11/2016 | Kaehler | |
| 2017/0007167 A1 | 1/2017 | Kostic et al. | |
| 2017/0231490 A1 | 8/2017 | Toth et al. | |
| 2017/0235931 A1 | 8/2017 | Publicover et al. | |

OTHER PUBLICATIONS

Al-Khalidi, F. Q., Saatchi, R., Burke, D., Elphick, H., & Tan, S. (2011). Respiration rate monitoring methods: A review. Pediatric pulmonology, 46(6), 523-529.

Appel, V. C., Belini, V. L., Jong, D. H., Magalhães, D. V., & Caurin, G. A. (Aug. 2014). Classifying emotions in rehabilitation robotics based on facial skin temperature. In Biomedical Robotics and Biomechatronics (2014 5th IEEE RAS & EMBS International Conference on (pp. 276-280). IEEE.

Aryal, A., Ghahramani, A., & Becerik-Gerber, B. (2017). Monitoring fatigue in construction workers using physiological measurements. Automation in Construction.

Boccanfuso, L., & O'Kane, J. M. (Jun. 2012). Remote measurement of breathing rate in real time using a high precision, single-point infrared temperature sensor. In Biomedical Robotics and Biomechatronics (BioRob), 2012 4th IEEE RAS & EMBS International Conference on (pp. 1704-1709). IEEE.

Cardone, D., Pinti, P., & Merla, A. (2015). Thermal infrared imaging-based computational psychophysiology for psychometrics. Computational and mathematical methods in medicine, 2015.

Carine Collé, Re-Experience Big-Data, 3 months group project with Sanya Rai Gupta and Florian Puech, UK, London, RCA, IDE, 2014, Amoeba.

Choi, J. S., Bang, J. W., Heo, H., & Park, K. R. (2015). Evaluation of Fear Using Nonintrusive Measurement of Multimodal Sensors. Sensors, 15(7), 17507-17533.

Clay-Warner, J., & Robinson, D. T. (2015). Infrared thermography as a measure of emotion response. Emotion Review, 7(2), 157-162.

Cross, C. B., Skipper, J. A., & Petkie, D. (May 2013). Thermal imaging to detect physiological indicators of stress in humans. In SPIE Defense, Security, and Sensing (pp. 87050I-87050I). International Society for Optics and Photonics.

Fei, J., & Pavlidis, I. (Aug. 2006). Analysis of breathing air flow patterns in thermal imaging. In Engineering in Medicine and Biology Society, 2006. EMBS'06. 28th Annual International Conference of the IEEE (pp. 946-952). IEEE.

Fei, J., & Pavlidis, I. (2010). Thermistor at a distance: unobtrusive measurement of breathing. IEEE Transactions on Biomedical Engineering, 57(4), 988-998.

(56) References Cited

OTHER PUBLICATIONS

Fernández-Cuevas, I., Marins, J. C. B., Lastras, J. A., Carmona, P. M. G., Cano, S. P., García-Concepción, M. Á., & Sillero-Quintana, M. (2015). Classification of factors influencing the use of infrared thermography in humans: A review. Infrared Physics & Technology, 71, 28-55.

Ghahramani, A., Castro, G., Becerik-Gerber, B., & Yu, X. (2016). Infrared thermography of human face for monitoring thermoregulation performance and estimating personal thermal comfort. Building and Environment, 109, 1-11.

Hawkes, P. W. (2012). Advances in Imaging and Electron Physics (vol. 171). Academic Press. Chapter 2.

Hong, K., Yuen, P., Chen, T., Tsitiridis, A., Kam, F., Jackman, J., . . . & Lightman+, F. T. S. (Sep. 2009). Detection and classification of stress using thermal imaging technique. In Proc. of SPIE Vol (vol. 7486, pp. 74860I-1).

Ioannou, S., Gallese, V., & Merla, A. (2014). Thermal infrared imaging in psychophysiology: potentialities and limits. Psychophysiology, 51(10), 951-963.

Jenkins, S. D., & Brown, R. D. H. (2014). A correlational analysis of human cognitive activity using Infrared Thermography of the supraorbital region, frontal EEG and self-report of core affective state. QIRT.

Johnson, M. L., Price, P. A., & Jovanov, E. (Aug. 2007). A new method for the quantification of breathing. In Engineering in Medicine and Biology Society, 2007. EMBS 2007. 29th Annual International Conference of the IEEE (pp. 4568-4571). IEEE.

Jovanov, E., Raskovic, D., & Hormigo, R. (2001). Thermistor-based breathing sensor for circadian rhythm evaluation. Biomedical sciences instrumentation, 37, 493-498.

Joyal, C. C., & Henry, M. (2013). Long-wave infrared functional brain imaging in human: a pilot study. The open neuroimaging journal, 7(1).

Kimura, S., Fukuomoto, M., & Horikoshi, T. (Sep. 2013). Eyeglass-based hands-free videophone. In Proceedings of the 2013 International Symposium on Wearable Computers (pp. 117-124). ACM.

Kurz, M., Hölzl, G., Riener, A., Anzengruber, B., Schmittner, T., & Ferscha, A. (Sep. 2012). Are you cool enough for Texas Hold'Em Poker?. In Proceedings of the 2012 ACM Conference on Ubiquitous Computing (pp. 1145-1149). ACM.

Lewis, G. F., Gatto, R. G., & Porges, S. W. (2011). A novel method for extracting respiration rate and relative tidal volume from infrared thermography. Psychophysiology, 48(7), 877-887.

Merla, A. (2014). Thermal expression of intersubjectivity offers new possibilities to human-machine and technologically mediated interactions.

Mizuno, T., & Kume, Y. (Aug. 2015). Development of a Glasses-Like Wearable Device to Measure Nasal Skin Temperature. In International Conference on Human-Computer Interaction (pp. 727-732). Springer International Publishing.

Mizuno, T., Sakai, T., Kawazura, S., Asano, H., Akehi, K., Matsuno, S., . . . & Itakura, N. (Jul. 2015). Facial Skin Temperature Fluctuation by Mental Work-Load with Thermography. In the International Conference on Electronics and Software Science (ICESS2015) Proceedings (pp. 212-215).

Murthy, R., & Pavlidis, I. (2006). Noncontact measurement of breathing function. IEEE Engineering in Medicine and Biology Magazine, 25(3), 57-67.

Murthy, R., Pavlidis, I., & Tsiamyrtzis, P. (Sep. 2004). Touchless monitoring of breathing function. In Engineering in Medicine arid Biology Society, 2004. IEMBS'04. 26th Annual International Conference of the IEEE (vol. 1, pp. 1196-1199). IEEE.

Nagaraj, S., Quoraishee, S., Chan, G., & Short, K. R. (Apr. 2010). Biometric study using hyperspectral imaging during stress. In SPIE Defense, Security, and Sensing (pp. 76740K-76740K). International Society for Optics and Photonics.

Nhan, B. R., & Chau, T. (2010). Classifying affective states using thermal infrared imaging of the human face. IEEE Transactions on Biomedical Engineering, 57(4), 979-987.

Pavlidis, I., & Levine, J. (2002). Thermal image analysis for polygraph testing. IEEE Engineering in Medicine and Biology Magazine, 21(6), 56-64.

Pavlidis, I., Dowdall, J., Sun, N., Puri, C., Fei, J., & Garbey, M. (2007). Interacting with human physiology. Computer Vision and Image Understanding, 108(1), 150-170.

Puri, C., Olson, L., Pavlidis, I., Levine, J., & Starren, J. (Apr. 2005). StressCam: non-contact measurement of users' emotional states through thermal imaging. In CHI'05 extended abstracts on Human factors in computing systems (pp. 1725-1728). ACM.

Rajoub, B. A., & Zwiggelaar, R. (2014). Thermal facial analysis for deception detection IEEE transactions on information forensics arid security, 9(6), 1015-1023.

Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).

Romera-Paredes, B., Zhang, C., & Zhang, Z. (Jul. 2014). Facial expression tracking from head-mounted, partially observing cameras. In Multimedia and Expo (ICME), 2014 IEEE International Conference on (pp. 1-6). IEEE.

Sharma, N., Dhall, A., Gedeon, T., & Goecke, R. (Sep. 2013). Modeling stress using thermal facial patterns: A spatio-temporal approach. In Affective Computing and Intelligent Interaction (ACII), 2013 Humaine Association Conference on (pp. 387-392). IEEE.

Sharma, N., Dhall, A., Gedeon, T., & Goecke, R. (2014). Thermal spatio-temporal data for stress recognition. EURASIP Journal on Image and Video Processing, 2014(1), 28.

Shastri, D., Papadakis, M., Tsiamyrtzis, P., Bass, B., & Pavlidis, I. (2012). Perinasal imaging of physiological stress and its affective potential. IEEE Transactions on Affective Computing, 3(3), 366-378.

Tsiamyrtzis, P., Dowdall, J., Shastri, D., Pavlidis, I. T., Frank, M. G., & Ekman, P. (2007). Imaging facial physiology for the detection of deceit. International Journal of Computer Vision, 71(2), 197-214.

Yang, M., Liu, Q., Turner, T., & Wu, Y. (Jun. 2008). Vital sign estimation from passive thermal video. In Computer Vision and Pattern Recognition, 2008. CVPR 2008. IEEE Conference on (pp. 1-8). IEEE.

Written opinion of the international searching authority, PCT/IB2017/056066, dated Jan. 29, 2018.

Written opinion of the international searching authority, PCT/IB2017/056067, dated Jan. 29, 2018.

Written opinion of the international searching authority, PCT/IB2017/056069, dated Jan. 29, 2018.

\* cited by examiner

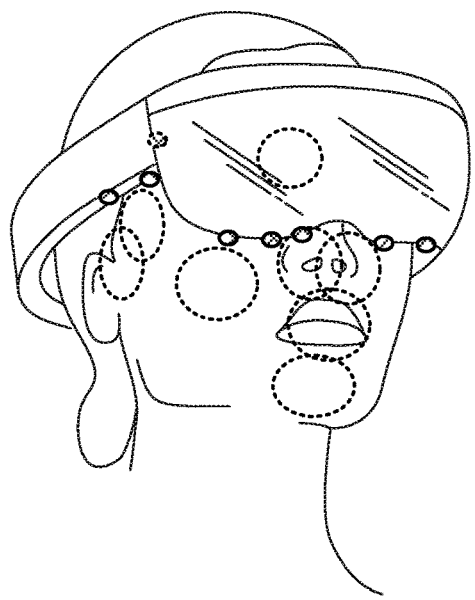 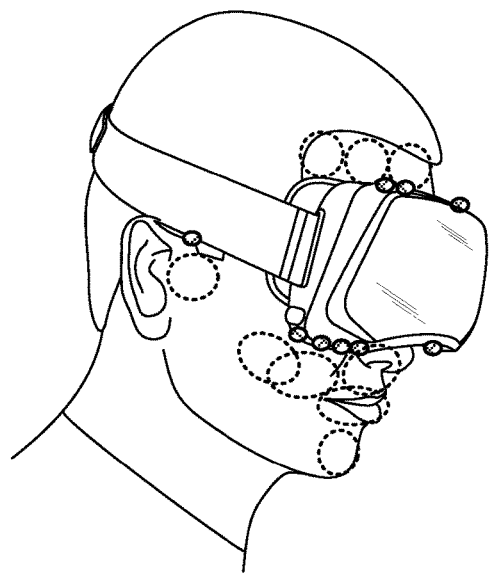
FIG. 2  FIG. 3
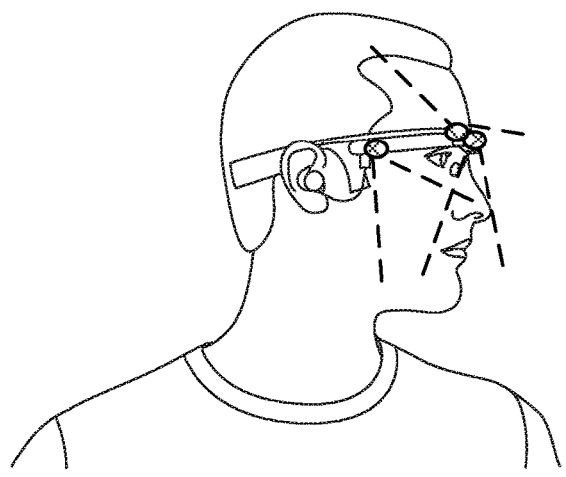 
FIG. 4  FIG. 5

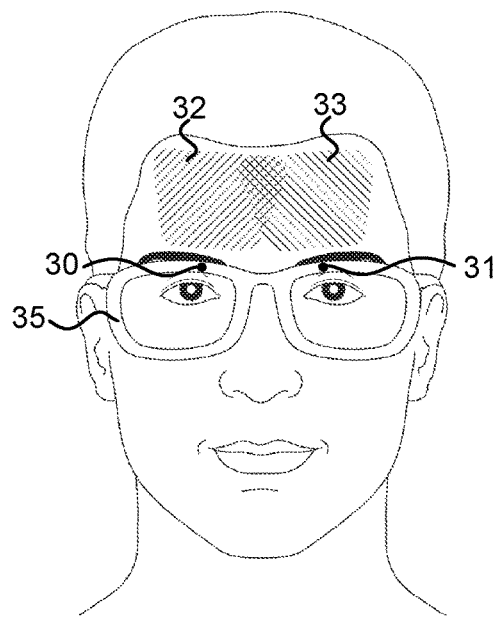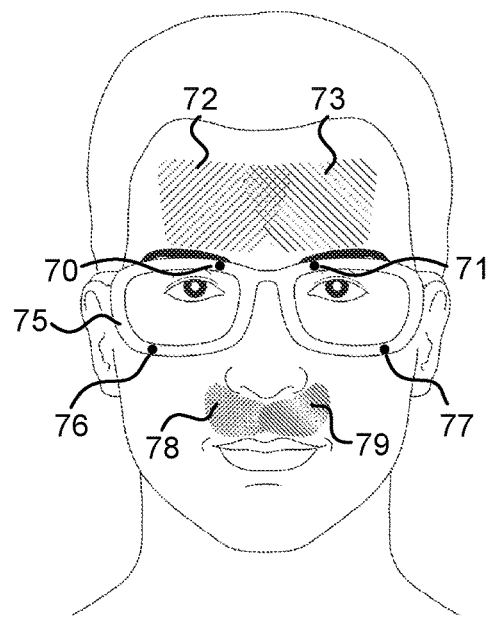
FIG. 6  FIG. 7
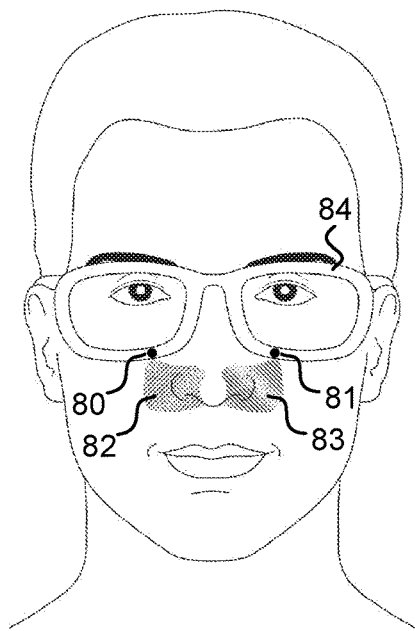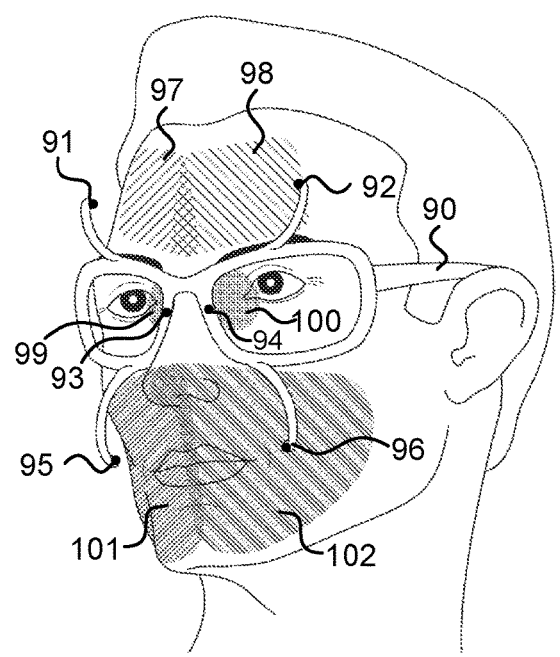
FIG. 8  FIG. 9

DETECTING IRREGULAR PHYSIOLOGICAL RESPONSES DURING EXPOSURE TO SENSITIVE DATA

CROSS-REFERENCE TO RELATED APPLICATIONS

This Application claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Provisional Patent Application No. 62/566,572 is herein incorporated by reference in its entirety.

This Application is also a Continuation-In-Part of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015.

This Application is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015.

This Application is also a Continuation-In-Part of U.S. application Ser. No. 15/284,528, filed Oct. 3, 2016, which claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

This Application is also a Continuation-In-Part of U.S. application Ser. No. 15/635,178, filed Jun. 27, 2017, which claims priority to U.S. Provisional Patent Application No. 62/354,833, filed Jun. 27, 2016, and U.S. Provisional Patent Application No. 62/372,063, filed Aug. 8, 2016.

This Application is also a Continuation-In-Part of U.S. application Ser. No. 15/722,434, filed Oct. 2, 2017, which claims priority to U.S. Provisional Patent Application No. 62/408,677, filed Oct. 14, 2016, and U.S. Provisional Patent Application No. 62/456,105, filed Feb. 7, 2017, and U.S. Provisional Patent Application No. 62/480,496, filed Apr. 2, 2017. U.S. Ser. No. 15/722,434 is also a Continuation-In-Part of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015. U.S. Ser. No. 15/722,434 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015. And U.S. Ser. No. 15/722,434 is also a Continuation-In-Part of U.S. application Ser. No. 15/284,528, filed Oct. 3, 2016, which claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

ACKNOWLEDGMENTS

Gil Thieberger would like to thank his holy and beloved teacher, Lama Dvora-hla, for her extraordinary teachings and manifestation of wisdom, love, compassion and morality, and for her endless efforts, support, and skills in guiding him and others on their paths to freedom and ultimate happiness. Gil would also like to thank his beloved parents for raising him exactly as they did.

BACKGROUND

Large and heavy non head-mounted thermal cameras are used today to measure physiological features like blood flow, pulse rate, blood vessels distribution, breathing rate, and to provide reliable cues indicative of deception. Because controlling ones physiological responses is difficult, facial thermal analysis can provide automatic deception detection accuracies above 85%. Instantaneous stress conditions can be detected using thermal imaging based on identifying an increase in the periorbital blood flow, and sustained stress conditions can be detected using thermal imaging based on identifying elevated blood flow in the forehead. However, none of the prior art techniques are used to control the access to sensitive data on a daily basis.

SUMMARY

Alertness, anxiety, and even fear are often experienced by people perpetrating illegal activities during their illicit actions. When a user experiences elevated feelings of alertness, anxiety, or fear, increased levels of adrenaline are secreted to regulate blood flow. Redistribution of blood flow in superficial blood vessels causes changes in local skin temperature that are apparent in the user's face. The changes to the blood flow are caused by the sympathetic system, and they usually cannot be totally controlled; thus, they may constitute a powerful biometric that is difficult to conceal. This biometric can provide valuable clues to security systems monitoring access to critical and/or sensitive data about potential suspects who are often not typically detected with identification biometrics, such as first time offenders.

In some embodiments, a user is permitted to access sensitive data through a head-mounted display (HMD) equipped with at least one thermal camera that measures temperature variations on the user's face while accessing the sensitive data. Optionally, accessing through the HMD is the only permitted access to the sensitive data. This way the user is under surveillance when accessing the sensitive data, and optionally there is no way for the user to access the sensitive data without being monitored by the system. Thus, if the user has an irregular physiological response while being exposed to the sensitive data, this event can be detected by the system.

One example of a system to detect an irregular physiological response while being exposed to sensitive data includes an HMD, an inward-facing head-mounted thermal camera (CAM), and a computer. The HMD is configured to expose sensitive data to the user who wears the HMD. The CAM is configured to take thermal measurements of a region of interest ($TH_{ROI}$) on the user's face while the user is exposed to the sensitive data, and is located less than 15 cm from the face. And the computer is configured to detect, based on certain $TH_{ROI}$ taken while the user was exposed to certain sensitive data, whether the user experienced the irregular physiological response while being exposed to the certain sensitive data.

BRIEF DESCRIPTION OF THE DRAWINGS

The embodiments are herein described by way of example only, with reference to the following drawings:

FIG. 2 illustrates inward-facing head-mounted cameras coupled to an augmented reality device;

FIG. 3 illustrates head-mounted cameras coupled to a virtual reality device;

FIG. 4 illustrates a side view of head-mounted cameras coupled to an augmented reality device;

FIG. 5 illustrates a side view of head-mounted cameras coupled to a sunglasses frame;

FIG. 6, FIG. 7, FIG. 8 and FIG. 9 illustrate head-mounted systems (HMSs) configured to measure various ROIs relevant to some of the embodiments describes herein;

DETAILED DESCRIPTION

Figure 1A:
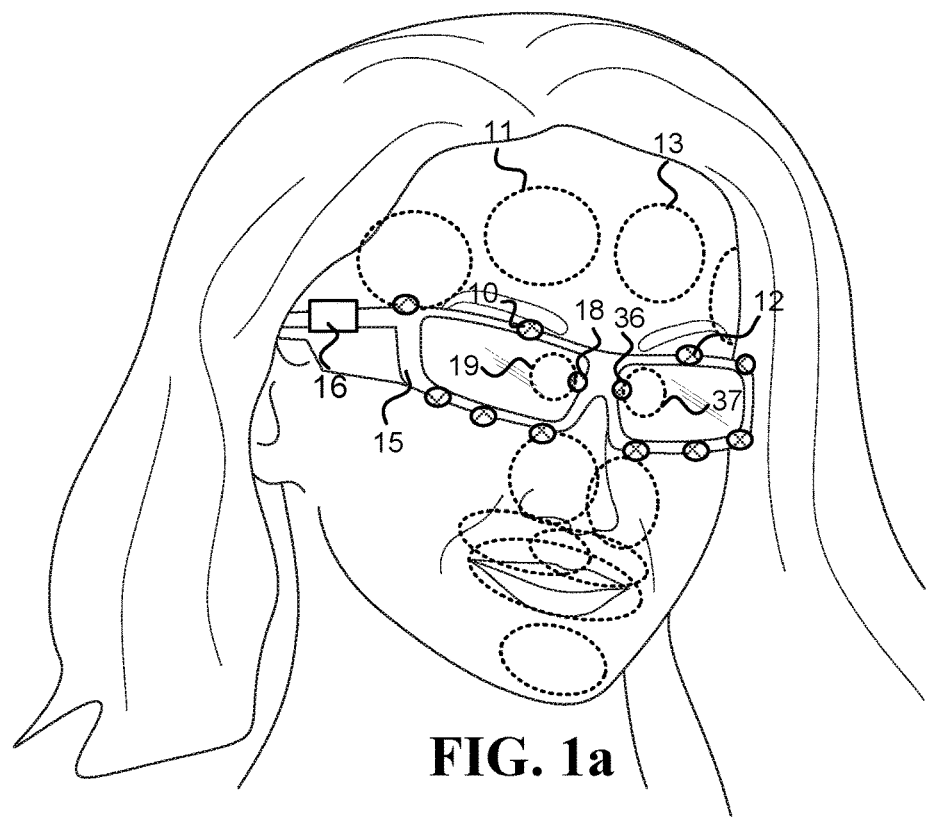
FIG. 1a and FIG. 1b illustrate various inward-facing head-mounted cameras coupled to an eyeglasses frame.

A "thermal camera" refers herein to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

Sentences in the form of "thermal measurements of an ROI" (usually denoted $TH_{ROI}$ or some variant thereof) refer to at least one of: (i) temperature measurements of the ROI ($T_{ROI}$), such as when using thermopile or microbolometer sensors, and (ii) temperature change measurements of the ROI ($\Delta T_{ROI}$), such as when using a pyroelectric sensor or when deriving the temperature changes from temperature measurements taken at different times by a thermopile sensor or a microbolometer sensor.

In some embodiments, a device, such as a thermal camera, may be positioned such that it occludes an ROI on the user's face, while in other embodiments, the device may be positioned such that it does not occlude the ROI. Sentences in the form of "the system/camera does not occlude the ROI" indicate that the ROI can be observed by a third person located in front of the user and looking at the ROI, such as illustrated by all the ROIs in FIG. 7 and FIG. 11. Sentences in the form of "the system/camera occludes the ROI" indicate that some of the ROIs cannot be observed directly by that third person, such as ROIs 19 and 37 that are occluded by the lenses in FIG. 1a, and ROIs 97 and 102 that are occluded by cameras 91 and 96, respectively, in FIG. 9.

Although many of the disclosed embodiments can use occluding thermal cameras successfully, in certain scenarios, such as when using an HMS on a daily basis and/or in a normal day-to-day setting, using thermal cameras that do not occlude their ROIs on the face may provide one or more advantages to the user, to the HMS, and/or to the thermal cameras, which may relate to one or more of the following: esthetics, better ventilation of the face, reduced weight, simplicity to wear, and reduced likelihood to being tarnished.

A "Visible-light camera" refers to a non-contact device designed to detect at least some of the visible spectrum, such as a camera with optical lenses and CMOS or CCD sensor.

The term "inward-facing head-mounted camera" refers to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be attached to eyeglass using a clip-on mechanism (configured to be attached to and detached from the eyeglasses), or may be mounted to the user's head using any other known device that keeps the camera in a fixed position relative to the user's head also when the head moves. Sentences in the form of "camera physically coupled to the frame" mean that the camera moves with the frame, such as when the camera is fixed to (or integrated into) the frame, or when the camera is fixed to (or integrated into) an element that is physically coupled to the frame. The abbreviation "CAM" denotes "inward-facing head-mounted thermal camera", the abbreviation "$CAM_{out}$" denotes "outward-facing head-mounted thermal camera", the abbreviation "VCAM" denotes "inward-facing head-mounted visible-light camera", and the abbreviation "$VCAM_{out}$" denotes "outward-facing head-mounted visible-light camera".

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frames in Google Glass™ and Spectacles by Snap Inc. are similar to eyeglasses frames. Additionally or alternatively, the frame may connect to, be affixed within, and/or be integrated with, a helmet (e.g., sports, motorcycle, bicycle, and/or combat helmets) and/or a brainwave-measuring headset.

When a thermal camera is inward-facing and head-mounted, challenges faced by systems known in the art that are used to acquire thermal measurements, which include non-head-mounted thermal cameras, may be simplified and even eliminated with some of the embodiments described herein. Some of these challenges may involve dealing with complications caused by movements of the user, image registration, ROI alignment, tracking based on hot spots or markers, and motion compensation in the IR domain.

In various embodiments, cameras are located close to a user's face, such as at most 2 cm, 5 cm, 10 cm, 15 cm, or 20 cm from the face (herein "cm" denotes to centimeters). The distance from the face/head in sentences such as "a camera located less than 15 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

Figure 1B:
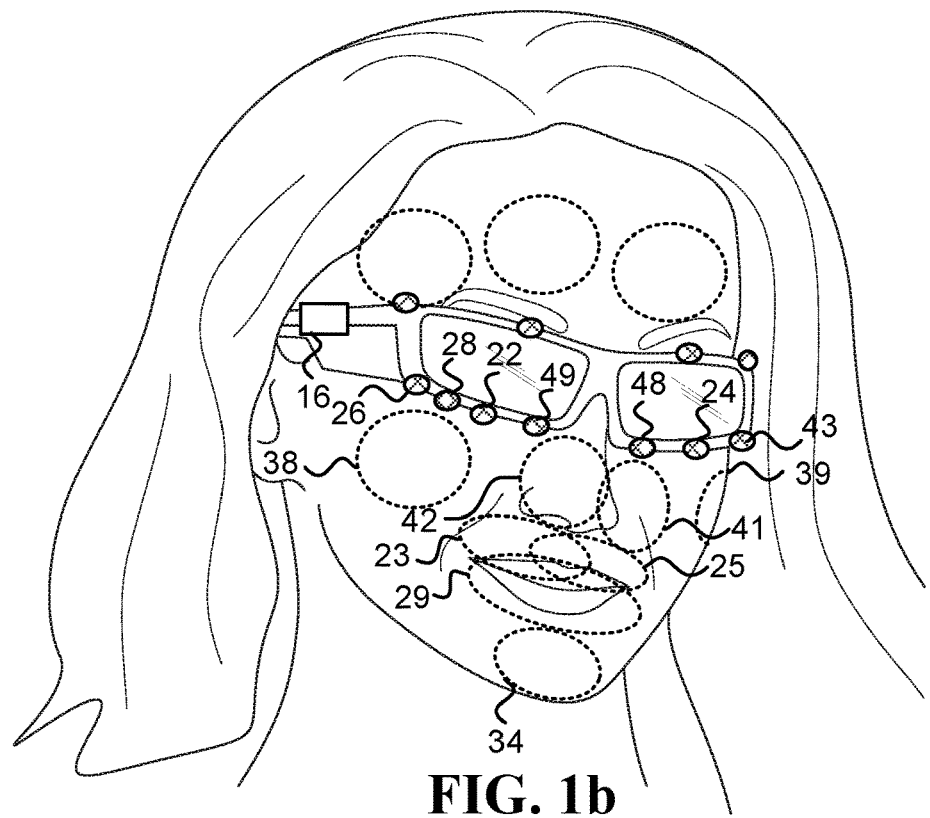

The following figures show various examples of HMSs equipped with head-mounted cameras. FIG. 1a illustrates various inward-facing head-mounted cameras coupled to an eyeglasses frame 15. Cameras 10 and 12 measure regions 11 and 13 on the forehead, respectively. Cameras 18 and 36 measure regions on the periorbital areas 19 and 37, respectively. The HMS further includes an optional computer 16, which may include a processor, memory, a battery and/or a communication module. FIG. 1b illustrates a similar HMS in which inward-facing head-mounted cameras 48 and 49 measure regions 41 and 41, respectively. Cameras 22 and 24 measure regions 23 and 25, respectively. Camera 28 measures region 29. And cameras 26 and 43 measure regions 38 and 39, respectively.

FIG. 2 illustrates inward-facing head-mounted cameras coupled to an augmented reality device such as Microsoft HoloLens™. FIG. 3 illustrates head-mounted cameras coupled to a virtual reality device such as Facebook's Oculus Rift™. FIG. 4 is a side view illustration of head-mounted cameras coupled to an augmented reality device such as Google Glass™. FIG. 5 is another side view illustration of head-mounted cameras coupled to a sunglasses frame.

FIG. 6 to FIG. 9 illustrate HMSs configured to measure various ROIs relevant to some of the embodiments describes herein. FIG. 6 illustrates a frame 35 that mounts inward-facing head-mounted cameras 30 and 31 that measure regions 32 and 33 on the forehead, respectively. FIG. 7 illustrates a frame 75 that mounts inward-facing head-mounted cameras 70 and 71 that measure regions 72 and 73 on the forehead, respectively, and inward-facing head-mounted cameras 76 and 77 that measure regions 78 and 79 on the upper lip, respectively. FIG. 8 illustrates a frame 84 that mounts inward-facing head-mounted cameras 80 and 81 that measure regions 82 and 83 on the sides of the nose, respectively. And FIG. 9 illustrates a frame 90 that includes (i) inward-facing head-mounted cameras 91 and 92 that are mounted to protruding arms and measure regions 97 and 98 on the forehead, respectively, (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Figure 10:
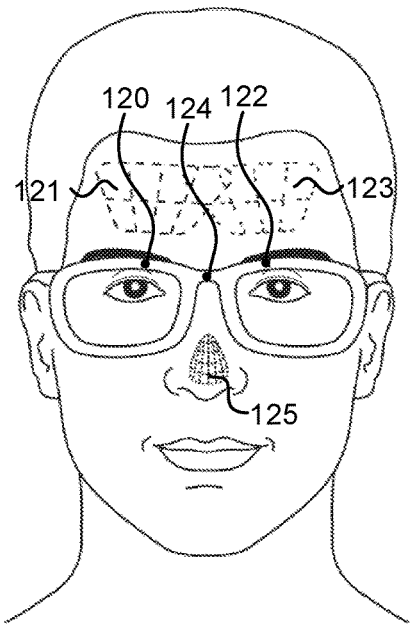
FIG. 10, FIG. 11, FIG. 12 and FIG. 13 illustrate various embodiments of systems that include inward-facing head-mounted cameras having multi-pixel sensors (FPA sensors)
Figure 11:
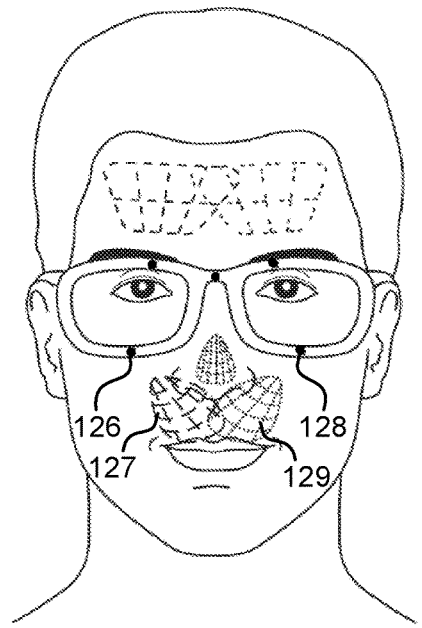
Figure 12:
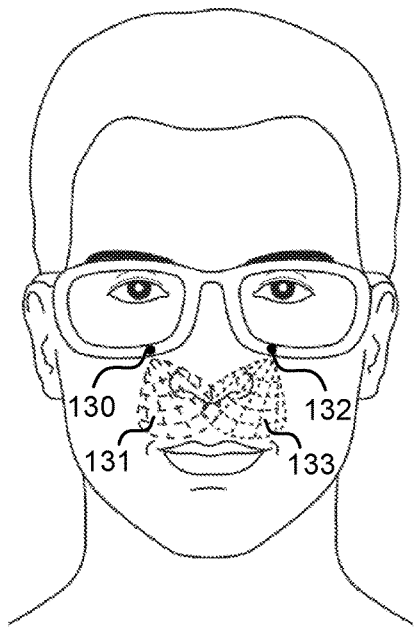
Figure 13:
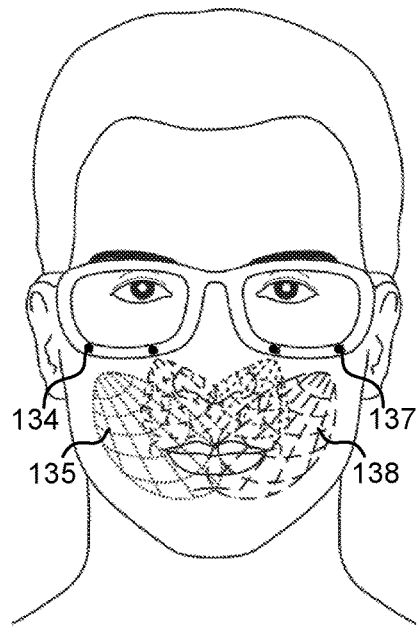

FIG. 10 to FIG. 13 illustrate various inward-facing head-mounted cameras having multi-pixel sensors (FPA sensors), configured to measure various ROIs relevant to some of the embodiments describes herein. FIG. 10 illustrates head-mounted cameras 120 and 122 that measure regions 121 and 123 on the forehead, respectively, and mounts head-mounted camera 124 that measure region 125 on the nose. FIG. 11 illustrates head-mounted cameras 126 and 128 that measure regions 127 and 129 on the upper lip, respectively, in addition to the head-mounted cameras already described in FIG. 10. FIG. 12 illustrates head-mounted cameras 130 and 132 that measure larger regions 131 and 133 on the upper lip and the sides of the nose, respectively. And FIG. 13 illustrates head-mounted cameras 134 and 137 that measure regions 135 and 138 on the right and left cheeks and right and left sides of the mouth, respectively, in addition to the head-mounted cameras already described in FIG. 12.

It is noted that the elliptic and other shapes of the ROIs in some of the drawings are just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a thermal camera is physically coupled, or by placing a LED instead of the sensor (while maintaining the same field of view) and observing the illumination pattern on the face. Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a CAM having just one pixel or a small number of pixels, the ROI may cover another area (in addition to the area). For example, a sentence in the form of "an ROI on the nose" may refer to either: 100% of the ROI is on the nose, or some of the ROI is on the nose and some of the ROI is on the upper lip.

Various embodiments described herein involve detections of physiological responses based on user measurements. Some examples of physiological responses include stress, an allergic reaction, an asthma attack, a stroke, dehydration, intoxication, or a headache (which includes a migraine). Other examples of physiological responses include manifestations of fear, startle, sexual arousal, anxiety, joy, pain or guilt. Still other examples of physiological responses include physiological signals such as a heart rate or a value of a respiratory parameter of the user. Optionally, detecting a physiological response may involve one or more of the following: determining whether the user has/had the physiological response, identifying an imminent attack associated with the physiological response, and/or calculating the extent of the physiological response.

In some embodiments, detection of the physiological response is done by processing thermal measurements that fall within a certain window of time that characterizes the physiological response. For example, depending on the physiological response, the window may be five seconds long, thirty seconds long, two minutes long, five minutes long, fifteen minutes long, or one hour long. Detecting the physiological response may involve analysis of thermal measurements taken during multiple of the above-described windows, such as measurements taken during different days. In some embodiments, a computer may receive a stream of thermal measurements, taken while the user wears an HMS with coupled thermal cameras during the day, and periodically evaluate measurements that fall within a sliding window of a certain size.

In some embodiments, models are generated based on measurements taken over long periods. Sentences of the form of "measurements taken during different days" or "measurements taken over more than a week" are not limited to continuous measurements spanning the different days or over the week, respectively. For example, "measurements taken over more than a week" may be taken by eyeglasses equipped with thermal cameras, which are worn for more than a week, 8 hours a day. In this example, the user is not required to wear the eyeglasses while sleeping in order to take measurements over more than a week. Similarly, sentences of the form of "measurements taken over more than 5 days, at least 2 hours a day" refer to a set comprising at least 10 measurements taken over 5 different days, where at least two measurements are taken each day at times separated by at least two hours.

Utilizing measurements taken of a long period (e.g., measurements taken on "different days") may have an advantage, in some embodiments, of contributing to the generalizability of a trained model. Measurements taken over the long period likely include measurements taken in different environments and/or measurements taken while the measured user was in various physiological and/or mental states (e.g., before/after meals and/or while the measured user was sleepy/energetic/happy/depressed, etc.). Training a model on such data can improve the performance of systems that utilize the model in the diverse settings often encountered in real-world use (as opposed to controlled laboratory-like settings). Additionally, taking the measurements over the long period may have the advantage of enabling collection of a large amount of training data that is required for some machine learning approaches (e.g., "deep learning").

Detecting the physiological response may involve performing various types of calculations by a computer. Optionally, detecting the physiological response may involve performing one or more of the following operations: comparing thermal measurements to a threshold (when the threshold is reached that may be indicative of an occurrence of the physiological response), comparing thermal measurements to a reference time series, and/or by performing calculations that involve a model trained using machine learning methods. Optionally, the thermal measurements upon which the one or more operations are performed are taken during a window of time of a certain length, which may optionally depend on the type of physiological response being detected. In one example, the window may be shorter than one or more of the following durations: five seconds, fifteen seconds, one minute, five minutes, thirty minute, one hour, four hours, one day, or one week. In another example, the window may be longer than one or more of the afore-mentioned durations. Thus, when measurements are taken over a long period, such as measurements taken over a period of more than a week, detection of the physiological response at a certain time may be done based on a subset of the measurements that falls within a certain window near the certain time; the detection at the certain time does not necessarily involve utilizing all values collected throughout the long period.

In some embodiments, detecting the physiological response of a user may involve utilizing baseline thermal measurement values, most of which were taken when the user was not experiencing the physiological response. Optionally, detecting the physiological response may rely on observing a change to typical temperatures at one or more ROIs (the baseline), where different users might have different typical temperatures at the ROIs (i.e., different baselines). Optionally, detecting the physiological response may rely on observing a change to a baseline level, which is determined based on previous measurements taken during the preceding minutes and/or hours.

In some embodiments, detecting a physiological response involves determining the extent of the physiological response, which may be expressed in various ways that are indicative of the extent of the physiological response, such as: (i) a binary value indicative of whether the user experienced, and/or is experiencing, the physiological response, (ii) a numerical value indicative of the magnitude of the physiological response, (iii) a categorial value indicative of the severity/extent of the physiological response, (iv) an expected change in thermal measurements of an ROI (denoted $TH_{ROI}$ or some variation thereof), and/or (v) rate of change in $TH_{ROI}$. Optionally, when the physiological response corresponds to a physiological signal (e.g., a heart rate, a breathing rate, and an extent of frontal lobe brain activity), the extent of the physiological response may be interpreted as the value of the physiological signal.

One approach for detecting a physiological response, which may be utilized in some embodiments, involves comparing thermal measurements of one or more ROIs to a threshold. In these embodiments, the computer may detect the physiological response by comparing the thermal measurements, and/or values derived therefrom (e.g., a statistic of the measurements and/or a function of the measurements), to the threshold to determine whether it is reached. Optionally, the threshold may include a threshold in the time domain, a threshold in the frequency domain, an upper threshold, and/or a lower threshold. When a threshold involves a certain change to temperature, the certain change may be positive (increase in temperature) or negative (decrease in temperature). Different physiological responses described herein may involve different types of thresholds, which may be an upper threshold (where reaching the threshold means≥the threshold) or a lower threshold (where reaching the threshold means≤the threshold); for example, each physiological response may involve at least a certain degree of heating, or at least a certain degree cooling, at a certain ROI on the face.

Another approach for detecting a physiological response, which may be utilized in some embodiments, may be applicable when the thermal measurements of a user are treated as time series data. For example, the thermal measurements may include data indicative of temperatures at one or more ROIs at different points of time during a certain period. In some embodiments, the computer may compare thermal measurements (represented as a time series) to one or more reference time series that correspond to periods of time in which the physiological response occurred. Additionally or alternatively, the computer may compare the thermal measurements to other reference time series corresponding to times in which the physiological response did not occur. Optionally, if the similarity between the thermal measurements and a reference time series corresponding to a physiological response reaches a threshold, this is indicative of the fact that the thermal measurements correspond to a period of time during which the user had the physiological response. Optionally, if the similarity between the thermal measurements and a reference time series that does not correspond to a physiological response reaches another threshold, this is indicative of the fact that the thermal measurements correspond to a period of time in which the user did not have the physiological response. Time series analysis may involve various forms of processing involving segmenting data, aligning data, clustering, time warping, and various functions for determining similarity between sequences of time series data. Some of the techniques that may be utilized in various embodiments are described in Ding, Hui, et al. "Querying and mining of time series data: experimental comparison of representations and distance measures." Proceedings of the VLDB Endowment 1.2 (2008): 1542-1552, and in Wang, Xiaoyue, et al. "Experimental comparison of representation methods and distance measures for time series data." Data Mining and Knowledge Discovery 26.2 (2013): 275-309.

Herein, "machine learning" methods refers to learning from examples using one or more approaches. Optionally, the approaches may be considered supervised, semi-supervised, and/or unsupervised methods. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using machine learning methods. For brevity's sake, at times, a "machine learning-based model" may simply be called a "model". Referring to a model as being "machine learning-based" is intended to indicate that the model is trained using machine learning methods (otherwise, "model" may also refer to a model generated by methods other than machine learning).

In some embodiments, which involve utilizing a machine learning-based model, a computer is configured to detect the physiological response by generating feature values based on the thermal measurements (and possibly other values), and/or based on values derived therefrom (e.g., statistics of the measurements). The computer then utilizes the machine learning-based model to calculate, based on the feature values, a value that is indicative of whether, and/or to what extent, the user is experiencing (and/or is about to experience) the physiological response. Optionally, calculating said value is considered "detecting the physiological response". Optionally, the value calculated by the computer is indicative of the probability that the user has/had the physiological response.

Herein, feature values may be considered input to a computer that utilizes a model to perform the calculation of a value, such as the value indicative of the extent of the physiological response mentioned above. It is to be noted that the terms "feature" and "feature value" may be used interchangeably when the context of their use is clear. However, a "feature" typically refers to a certain type of value, and represents a property, while "feature value" is the value of the property with a certain instance (sample). For example, a feature may be temperature at a certain ROI, while the feature value corresponding to that feature may be 36.9° C. in one instance and 37.3° C. in another instance.

In some embodiments, a machine learning-based model used to detect a physiological response is trained based on data that includes samples. Each sample includes feature values and a label. The feature values may include various types of values. At least some of the feature values of a sample are generated based on measurements of a user taken during a certain period of time (e.g., thermal measurements taken during the certain period of time). Optionally, some of the feature values may be based on various other sources of information described herein. The label is indicative of a physiological response of the user corresponding to the certain period of time. Optionally, the label may be indicative of whether the physiological response occurred during the certain period and/or the extent of the physiological response during the certain period. Additionally or alternatively, the label may be indicative of how long the physiological response lasted. Labels of samples may be generated using various approaches, such as self-report by users, annotation by experts that analyze the training data, automatic annotation by a computer that analyzes the training data and/or analyzes additional data related to the training data, and/or utilizing additional sensors that provide data useful for generating the labels. It is to be noted that herein when it is stated that a model is trained based on certain measurements (e.g., "a model trained based on $TH_{ROI}$ taken on different days"), it means that the model was trained on samples comprising feature values generated based on the certain measurements and labels corresponding to the certain measurements. Optionally, a label corresponding to a measurement is indicative of the physiological response at the time the measurement was taken.

Various types of feature values may be generated based on thermal measurements. In one example, some feature values are indicative of temperatures at certain ROIs. In another example, other feature values may represent a temperature change at certain ROIs. The temperature changes may be with respect to a certain time and/or with respect to a different ROI. In order to better detect physiological responses that take some time to manifest, in some embodiments, some feature values may describe temperatures (or temperature changes) at a certain ROI at different points of time. Optionally, these feature values may include various functions and/or statistics of the thermal measurements such as minimum/maximum measurement values and/or average values during certain windows of time.

It is to be noted that when it is stated that feature values are generated based on data comprising multiple sources, it means that for each source, there is at least one feature value that is generated based on that source (and possibly other data). For example, stating that feature values are generated from thermal measurements of first and second ROIs ($TH_{ROI1}$ and $TH_{ROI2}$, respectively) means that the feature values may include a first feature value generated based on $TH_{ROI1}$ and a second feature value generated based on $TH_{ROI2}$. Optionally, a sample is considered generated based on measurements of a user (e.g., measurements comprising $TH_{ROI1}$ and $TH_{ROI2}$) when it includes feature values generated based on the measurements of the user.

In addition to feature values that are generated based on thermal measurements, in some embodiments, at least some feature values utilized by a computer (e.g., to detect a physiological response or train a mode) may be generated based on additional sources of data that may affect temperatures measured at various facial ROIs. Some examples of the additional sources include: (i) measurements of the environment such as temperature, humidity level, noise level, elevation, air quality, a wind speed, precipitation, and infrared radiation; (ii) contextual information such as the time of day (e.g., to account for effects of the circadian rhythm), day of month (e.g., to account for effects of the lunar rhythm), day in the year (e.g., to account for seasonal effects), and/or stage in a menstrual cycle; (iii) information about the user being measured such as sex, age, weight, height, and/or body build. Alternatively or additionally, at least some feature values may be generated based on physiological signals of the user obtained by sensors that are not thermal cameras, such as a visible-light camera, a photoplethysmogram (PPG) sensor, an electrocardiogram (ECG) sensor, an electroencephalography (EEG) sensor, a galvanic skin response (GSR) sensor, or a thermistor.

The machine learning-based model used to detect a physiological response may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects different conditions can have on the values of thermal measurements, and consequently, be able to achieve better detection of the physiological response in real world day-to-day scenarios.

Since real world day-to-day conditions are not the same all the time, sometimes detection of the physiological response may be hampered by what is referred to herein as "confounding factors". A confounding factor can be a cause of warming and/or cooling of certain regions of the face, which is unrelated to a physiological response being detected, and as such, may reduce the accuracy of the detection of the physiological response. Some examples of confounding factors include: (i) environmental phenomena such as direct sunlight, air conditioning, and/or wind; (ii) things that are on the user's face, which are not typically there and/or do not characterize the faces of most users (e.g., cosmetics, ointments, sweat, hair, facial hair, skin blemishes, acne, inflammation, piercings, body paint, and food leftovers); (iii) physical activity that may affect the user's heart rate, blood circulation, and/or blood distribution (e.g., walking, running, jumping, and/or bending over); (iv) consumption of substances to which the body has a physiological response that may involve changes to temperatures at various facial ROIs, such as various medications, alcohol, caffeine, tobacco, and/or certain types of food; and/or (v) disruptive facial movements (e.g., frowning, talking, eating, drinking, sneezing, and coughing).

Occurrences of confounding factors may not always be easily identified in thermal measurements. Thus, in some embodiments, systems may incorporate measures designed to accommodate for the confounding factors. In some embodiments, these measures may involve generating feature values that are based on additional sensors, other than the thermal cameras. In some embodiments, these measures may involve refraining from detecting the physiological response, which should be interpreted as refraining from providing an indication that the user has the physiological response. For example, if an occurrence of a certain confounding factor is identified, such as strong directional sunlight that heats one side of the face, the system may refrain from detecting that the user had a stroke. In this example, the user may not be alerted even though a temperature difference between symmetric ROIs on both sides of the face reaches a threshold that, under other circumstances, would warrant alerting the user.

Training data used to train a model for detecting a physiological response may include, in some embodiments, a diverse set of samples corresponding to various conditions, some of which involve occurrence of confounding factors (when there is no physiological response and/or when there is a physiological response). Having samples in which a confounding factor occurs (e.g., the user is in direct sunlight or touches the face) can lead to a model that is less susceptible to wrongfully detect the physiological response (which may be considered an occurrence of a false positive) in real world situations.

When a model is trained with training data comprising samples generated from measurements of multiple users, the model may be considered a general model. When a model is trained with training data comprising at least a certain proportion of samples generated from measurements of a certain user, and/or when the samples generated from the measurements of the certain user are associated with at least a certain proportion of weight in the training data, the model may be considered a personalized model for the certain user. Optionally, the personalized model for the certain user provides better results for the certain user, compared to a general model that was not personalized for the certain user. Optionally, personalized model may be trained based on measurements of the certain user, which were taken while the certain user was in different situations; for example, train the model based on measurements taken while the certain user had a headache/epilepsy/stress/anger attack, and while the certain user did not have said attack. Additionally or alternatively, the personalized model may be trained based on measurements of the certain user, which were taken over a duration long enough to span different situations; examples of such long enough durations may include: a week, a month, six months, a year, and three years.

Training a model that is personalized for a certain user may require collecting a sufficient number of training samples that are generated based on measurements of the certain user. Thus, initially detecting the physiological response with the certain user may be done utilizing a general model, which may be replaced by a personalized model for the certain user, as a sufficiently large number of samples are generated based on measurements of the certain user. Another approach involves gradually modifying a general model based on samples of the certain user in order to obtain the personalized model.

After a model is trained, the model may be provided for use by a system that detects the physiological response. Providing the model may involve performing different operations. In one embodiment, providing the model to the system involves forwarding the model to the system via a computer network and/or a shared computer storage medium (e.g., writing the model to a memory that may be accessed by the system that detects the physiological response). In another embodiment, providing the model to the system involves storing the model in a location from which the system can retrieve the model, such as a database and/or cloud-based storage from which the system may retrieve the model. In still another embodiment, providing the model involves notifying the system regarding the existence of the model and/or regarding an update to the model. Optionally, this notification includes information needed in order for the system to obtain the model.

A model for detecting a physiological response may include different types of parameters. Following are some examples of various possibilities for the model and the type of calculations that may be accordingly performed by a computer in order to detect the physiological response: (a) the model comprises parameters of a decision tree. Optionally, the computer simulates a traversal along a path in the decision tree, determining which branches to take based on the feature values. A value indicative of the physiological response may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of the physiological response; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of the physiological response.

A user interface (UI) may be utilized, in some embodiments, to notify the user and/or some other entity, such as a caregiver, about the physiological response and/or present an alert responsive to an indication that the extent of the physiological response reaches a threshold. The UI may include a screen to display the notification and/or alert, a speaker to play an audio notification, a tactile UI, and/or a vibrating UI. In some embodiments, "alerting" about a physiological response of a user refers to informing about one or more of the following: the occurrence of a physiological response that the user does not usually have (e.g., a stroke, intoxication, and/or dehydration), an imminent physiological response (e.g., an allergic reaction, an epilepsy attack, and/or a migraine), and an extent of the physiological response reaching a threshold (e.g., stress and/or anger reaching a predetermined level).

Some of the disclosed embodiments may be utilized to detect a stress level of a user based on thermal measurements of the user's face, such as the periorbital areas (i.e., areas around the eyes). In one embodiment, a system configured to detect a stress level includes a CAM and a computer. CAM takes thermal measurements of a region on a periorbital area ($TH_{ROI1}$) of the user, and is located less than 10 cm from the user's head. The computer detects the stress level based on $TH_{ROI1}$.

In one embodiment, in which the region is on the periorbital area of the right eye, the system further includes a second inward-facing head-mounted thermal camera (CAM2), which is located less than 10 cm from the user's head and takes thermal measurements of a region on the periorbital area of the left eye ($TH_{ROI2}$). Optionally, the computer detects the stress level based on both $TH_{ROI1}$ and $TH_{ROI2}$. Optionally, CAM and CAM2 are located at least 0.5 cm to the right and to the left of the vertical symmetry axis (which goes through the middle of the forehead and the middle of the nose), respectively. Optionally, each of CAM and CAM2 weighs below 10 g and is based on a thermopile, a microbolometer, or a pyroelectric sensor, which may be a focal-plane array sensor.

It is to be noted that while various embodiments may utilize a single CAM, due to asymmetrical placement of blood vessels in the face, thermal emissions of faces of many people are asymmetric to a certain extent. That is, the pattern of thermal emission from the left side of the face may be different (possibly even noticeably different) from the pattern of thermal emission from the right side of the face. Thus, for example, the temperature changes at the periorbital areas, in response to experiencing at least a certain level of stress, may be asymmetric for some users. The fact that various embodiments described below may include two (or more) CAMs that take measurements of ROIs covering different sides of the face (referred to as $TH_{ROI1}$ and $TH_{ROI2}$) can enable the computer to account for the thermal asymmetry when detecting the stress level.

In some cases, interferences (such as an external heat source, touching one of the eyes, or an irritated eye) cause an asymmetric effect on the right and left periorbital areas. As a result, utilizing right and left CAMs, which are located in different angles relative to the interfering source, provides the computer additional data that can improve its performances. The following are some examples of various ways in which the computer may account for the asymmetry when detecting the stress level based on $TH_{ROI1}$ and $TH_{ROI2}$, which include measurements of the of regions on the periorbital areas of the right and left eyes of the user, respectively.

In one embodiment, when comparing $TH_{ROI1}$ and $TH_{ROI2}$ to thresholds, the computer may utilize different thresholds for $TH_{ROI1}$ and $TH_{ROI2}$, in order to determine whether the user experienced a certain level of stress. Optionally, the different thresholds may be learned based on previous $TH_{ROI1}$ and $TH_{ROI2}$, which were measured when the user experienced the certain level of stress and/or suffered from certain interferences.

In another embodiment, the computer may utilize different reference time series to which $TH_{ROI1}$ and $TH_{ROI2}$ are compared in order to determine whether the user experienced the certain level of stress. Optionally, accounting for the asymmetric manifestation of the stress is reflected in the fact that a reference time series to which $TH_{ROI1}$ is compared is different from a reference time series to which $TH_{ROI2}$ is compared.

In yet another embodiment, when the computer utilizes a model to calculate a stress level based on feature values generated based on $TH_{ROI1}$ and/or $TH_{ROI2}$. Optionally, the feature values include: (i) at least first and second feature values generated based on $TH_{ROI1}$ and $TH_{ROI2}$, respectively; and/or (ii) a third feature value indicative of the magnitude of a difference between $TH_{ROI1}$ and $TH_{ROI2}$. In this embodiment, the computer may provide different results for first and second events that involve the same average change in $TH_{ROI1}$ and $TH_{ROI2}$, but with different extents of asymmetry between $TH_{ROI1}$ and $TH_{ROI2}$, and/or different magnitudes of interferences on the right and left eyes.

In still another embodiment, the computer may utilize the fact that asymmetric temperature changes occur when the user experiences stress in order to distinguish between stress and other causes of temperature changes in the periorbital areas. For example, drinking a hot beverage or having a physical exercise may cause in some people a more symmetric warming pattern to the periorbital areas than stress. Thus, if such a more symmetric warming pattern is observed, the computer may refrain from identifying the temperature changes as being stress-related. However, if the warming pattern is asymmetric and corresponds to temperature changes in the periorbital areas of the user when the user experiences stress, then the computer may identify the changes in the temperatures being stress-related.

The computer may employ different approaches when detecting the stress level based on $TH_{ROI1}$ (and possibly other sources of data such as $TH_{ROI2}$). In one embodiment, the computer may compare $TH_{ROI1}$ (and possibly other data) to a threshold(s), which when reached would indicate a certain stress level. In another embodiment, the computer may generate feature values based on $TH_{ROI1}$ and $TH_{ROI2}$, and utilize a model (also referred to as a "machine learning-based model") to calculate a value indicative of the stress level based on the feature values (calculating the value indicative of the stress level may be considered herein as "detecting the stress level"). At least some of the feature values are generated based on $TH_{ROI1}$. Optionally, at least some of the feature values may be generated based on other sources of data, such as $TH_{ROI1}$ and/or $TH_{ROI2}$ (described below). Optionally, the model was trained based on samples comprising feature values generated based on previous $TH_{ROI1}$ (and possibly other data, as explained below), and corresponding labels indicative of a stress level of the user. Optionally, the data used to train the model includes previous $TH_{ROI1}$ taken while the user was under elevated stress, and other previous $TH_{ROI1}$ taken while the user was not under elevated stress. Optionally, "elevated stress" refers to a stress level that reaches a certain threshold, where the value of the threshold is set according to a predetermined stress scale (examples of stress scales are given further below). Optionally, "elevated stress" refers to a physiological state defined by certain threshold values of physiological signals (e.g., pulse, breathing rate, and/or concentration of cortisol in the blood).

In a first embodiment, when the stress level exceeds a certain value, $TH_{ROI1}$ reach a threshold, and when the stress level does not exceed the certain value, $TH_{ROI1}$ do not reach the threshold. Optionally, the stress level is proportional to the values of $TH_{ROI1}$ (which are thermal measurements of the region on the periorbital area), such that the higher $TH_{ROI1}$ and/or the higher the change to $TH_{ROI1}$ (e.g., with reference to a baseline), the higher the stress level.

In a second embodiment, the computer detects the stress level based on a difference between $TH_{ROI1}$ and a baseline value determined based on a set of previous measurements taken by CAM. Optionally, most of the measurements belonging to the set were taken while the user was not under elevated stress.

In a third embodiment, the stress level is detected using a model and feature values generated based on additional measurements ($m_{conf}$) of the user and/or of the environment in which the user was in while $TH_{ROI1}$ were taken. $m_{conf}$ may be taken by sensor 461. Optionally, $m_{conf}$ are indicative of an extent to which a confounding factor occurred while $TH_{ROI1}$ were taken. The following are some examples of sources of information for $m_{conf}$, which may be used to detect the stress level.

In a first example, $m_{conf}$ are physiological signals such as a heart rate, heart rate variability, galvanic skin response, a respiratory rate, and respiratory rate variability, which are taken using sensors such as PPG, ECG, EEG, GSR and/or a thermistor.

In a second example, $m_{conf}$ represent an environmental condition and/or a situation of the user that may be considered a confounding factor, such as an indication of whether the user touched at least one of the eyes, an indication of whether the user is engaged in physical activity (and possibly the type and/or extent of the physical activity), temperature, humidity, IR radiation level, and a noise level. Optionally, the one or more values are obtained based on using an accelerometer, a pedometer, a humidity sensor, a miniature radar (such as low-power radar operating in the range between 30 GHz and 3,000 GHz), a miniature active electro-optics distance measurement device (such as a miniature Lidar), an anemometer, an acoustic sensor, and/or a light meter.

In a third example, $m_{conf}$ represent properties describing the user, such as the user's age, gender, marital status, occupation, education level, health conditions, and/or mental health issues that the user may have.

Stress may be thought of as the body's method of reacting to a challenge. Optionally, stress may be considered a physiological reaction to a stressor. Some examples of stressors include mental stressors that may include, but are not limited to, disturbing thoughts, discontent with something, events, situations, individuals, comments, or anything a user may interpret as negative or threatening. Other examples of stressors include physical stressors that may put strain on the body (e.g., very cold/hot temperatures, injury, chronic illness, or pain). In one example, a (high) workload may be considered a stressor. The extent to which a user feels stressed is referred to herein as a "stress level" and being under a certain level of stress may be referred to herein as "experiencing a certain stress level". Depending on the embodiment, a stress level may be expressed via various types of values, such as a binary value (the user is "stressed" or "not stressed", or the user is under "elevated stress" or "not under elevated stress"), a categorial value (e.g., no stress/low stress/medium stress/high stress), and/or a numerical value (e.g., a value on a scale of 0 to 10). In some embodiments, a "stress level" may refer to a "fight or flight" reaction level.

Evaluation of stress typically involves determining an amount of stress a person may be feeling according to some standard scale. There are various approaches known in the literature that may be used for this task. One approach involves identifying various situations the person may be in, which are associated with certain predefined extents of stress (which are empirically derived based on observations). Example of popular approaches include the Holmes and Rahe stress scale, the Perceived Stress Scale, and the Standard Stress Scale (SSS). A common trait of many the various stress scales is that they require a manual evaluation of situations a user undergoes, and do not measure the actual physiological effects of stress.

In some embodiments, the computer may receive an indication of a type of stressor, and utilize the indication to detect the stress level. Optionally, the indication is indicative of a period and/or duration during which the user was affected by the stressor. In one example, the indication is utilized to select a certain threshold value, which is appropriate for the type of stressor, and to which $TH_{ROI1}$ may be compared in order to determine whether the user is experiencing a certain stress level. Optionally, the certain threshold is determined based on thermal measurements of the user when the user reacted to a stressor of the indicated type. In another example, the indication is utilized to select a certain reference time series, which corresponds to the type of stressor, and to which $TH_{ROI1}$ may be compared in order to determine whether the user is experiencing a certain stress level. Optionally, the certain time series is based on thermal measurements of the user taken when the user reacted to a stressor of the indicated type. In yet another example, the computer generates one or more feature values based on the indication, and the one or more feature values are utilized to detect the stress level using a model (in addition to feature values generated based on $TH_{ROI1}$). In still another example, the computer may select a window of time based on the indication, which corresponds to the expected duration of stress induced by the type of stressor indicated in the indication. In this example, in order to detect the stress level of the user, the computer evaluates thermal measurements from among $TH_{ROI1}$ that were taken at a time that falls in the window.

Additional CAMs may be utilized to detect the stress level. The thermal measurements of the additional CAMs, typically denoted $TH_{ROIi}$ below, may be utilized to generate one or more of the feature values that are used along with the machine learning-based model to detect the stress level.

In one embodiment, the system includes a second inward-facing head-mounted thermal camera (CAM2) that takes thermal measurements of an additional ROI on the face ($TH_{ROI2}$), such as the forehead, the nose, and/or a region below the nostrils. The region below the nostrils refer to one or more regions on the upper lip, the mouth, and/or air volume through which the exhale streams from the nose and/or mouth flow, and it's thermal measurements are indicative of the user's breathing.

Given $TH_{ROI2}$, the computer may generate feature values based on $TH_{ROI1}$ and $TH_{ROI2}$ (and possibly other sources of data) and utilizes a model to detect the stress level based on the feature values. Optionally, the model was trained based on previous $TH_{ROI1}$ and $TH_{ROI2}$ taken while the user had at least two different stress levels according to a predetermined stress scale. For example, a first set of previous $TH_{ROI1}$ and $TH_{ROI2}$ taken while the user was under elevated stress, and a second set of previous $TH_{ROI2}$ and $TH_{ROI1}$ taken while the user was not under elevated stress.

In another embodiment, the system further includes second and third CAMs that take thermal measurements of regions on the right and left cheeks, respectively. Optionally, the computer detects the stress level also based on the thermal measurements of the cheeks.

Figure 15:
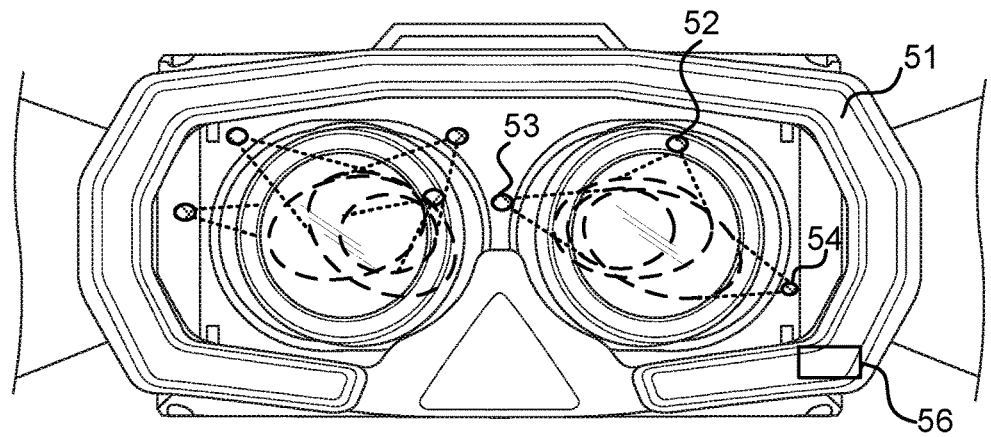
FIG. 15 illustrates an embodiment of an HMS able to measure stress level.

FIG. 15 illustrates one embodiment of an HMS able to measure stress level. The system includes a frame 51, CAMs (52, 53, 54), and a computer 56. CAMs are physically coupled to the frame and take thermal measurements of ROIs on the periorbital areas. Because CAMs are located close to their respective ROIs, they can be small, lightweight, and may be placed in many potential locations having line of sight to their respective ROIs. The computer 56, which may by located on the HMS, worn by the user, and/or remote such as in the cloud, detects the stress level based on changes to temperature of the periorbital areas received from the CAMs.

Due to the asymmetry of blood vessels in human faces and different shapes of human faces, having CAMs pointed at the right and left periorbital areas may enable a more accurate detection of physiological phenomena such as stress, and/or may enable detection of stress that is harder to detect based on measuring only a single periorbital area.

Figure 16:
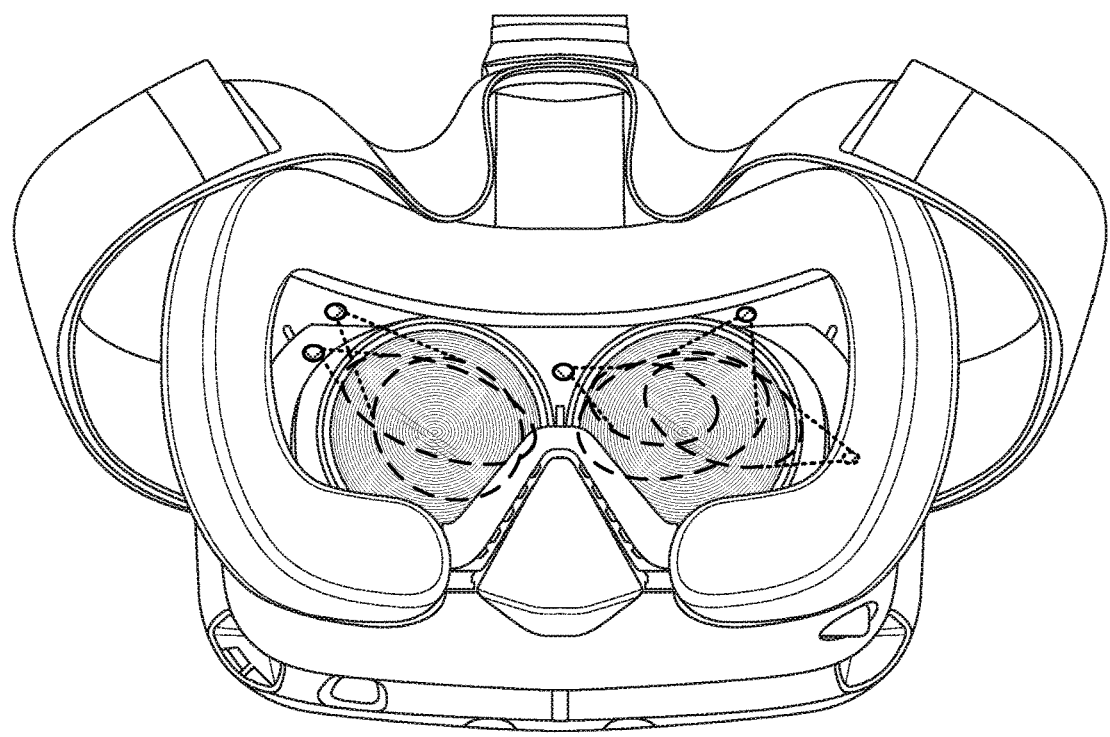
FIG. 16 illustrates examples of asymmetric locations of inward-facing head-mounted thermal cameras (CAMs) that measure the periorbital areas.
Figure 17:
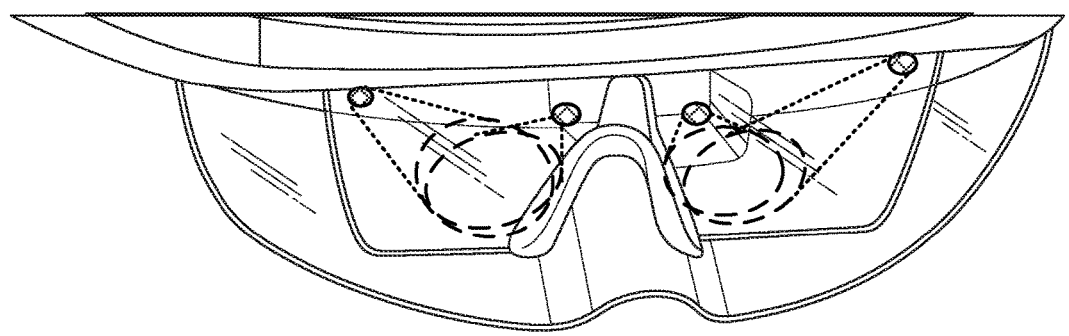
FIG. 17 illustrates an example of symmetric locations of CAMs that measure the periorbital areas.

While FIG. 15 and FIG. 16 illustrate examples of asymmetric locations of CAMs that measure the right periorbital area relative to the locations of CAMs that measure the left periorbital area, FIG. 17 illustrates an example of symmetric locations of the CAMs that measure the right periorbital area relative to the locations of the CAMs that measure the left periorbital area. In some embodiments, using thermal measurements from both symmetric and asymmetric located CAMs may improve the system's adaptability to different faces having different proportions.

Figure 19A:
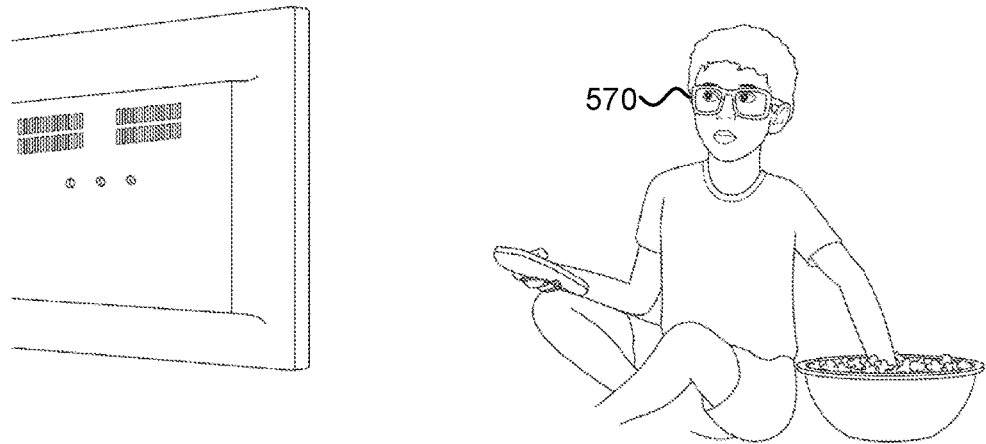
FIG. 19a illustrates a child watching a movie while wearing an eyeglasses frame with at least five CAMs.
Figure 19B:
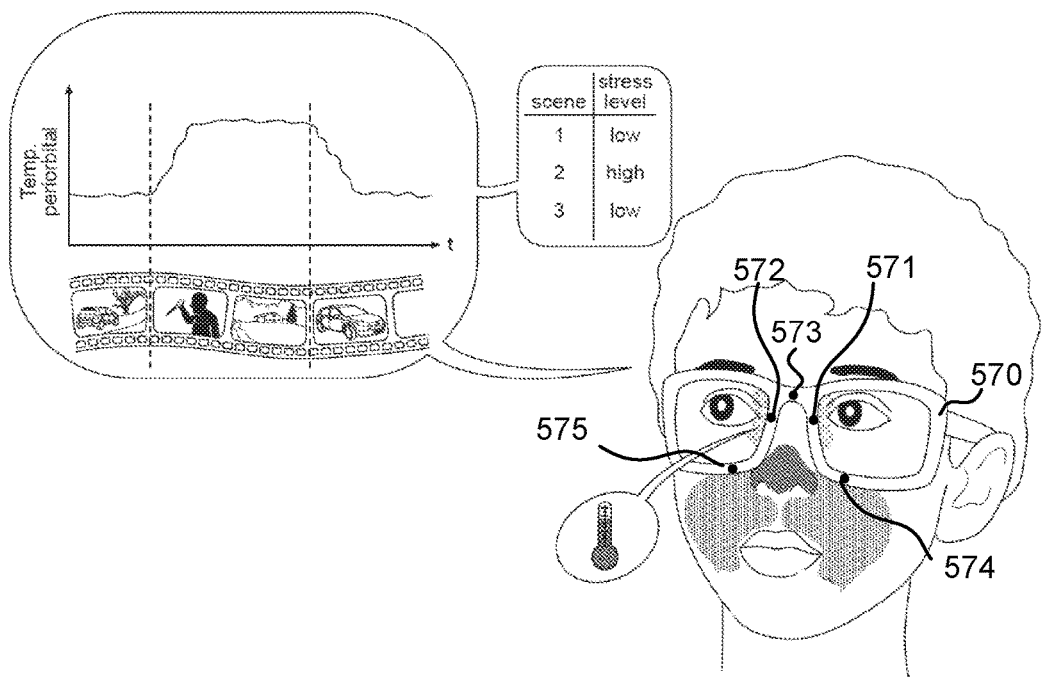
FIG. 19b illustrates generation of a graph of the stress level of the child detected at different times while different movie scenes were viewed.

FIG. 19a and FIG. 19b illustrate one scenario of detecting a user's stress level. FIG. 19a illustrates a child watching a movie while wearing an eyeglasses frame 570 with at least five CAMs. FIG. 19b illustrates the at least five CAMs 571, 572, 573, 574, and 575, which measure the right and left periorbital areas, the nose, and the right and left cheeks, respectively (the different ROIs are designated by different patterns). The figure further illustrates how the system produces a graph of the stress level detected at different times while different movie scenes were viewed.

In one embodiment, the system may include a head-mounted display (HMD) that presents digital content to the user and does not prevent CAM from measuring the ROI. In another embodiment, the system may include an eye tracker to track the user's gaze, and an optical see through HMD that operates in cooperation with the following components: a visible-light camera that captures images of objects the user is looking at, and a computer that matches the objects the user is looking at with the detected stress levels. Optionally, the eye tracker is coupled to a frame worn by the user. In yet another embodiment, the system may include a HMD that presents video comprising objects, and an eye tracker. The computer utilizes data generated by the eye tracker to match the objects the user is looking at with the detected stress levels. It is to be noted that there may be a delay between being affected by a stressor and a manifestation of stress as a reaction, and this delay may be taken into account when determining what objects caused the user stress.

Figure 21:
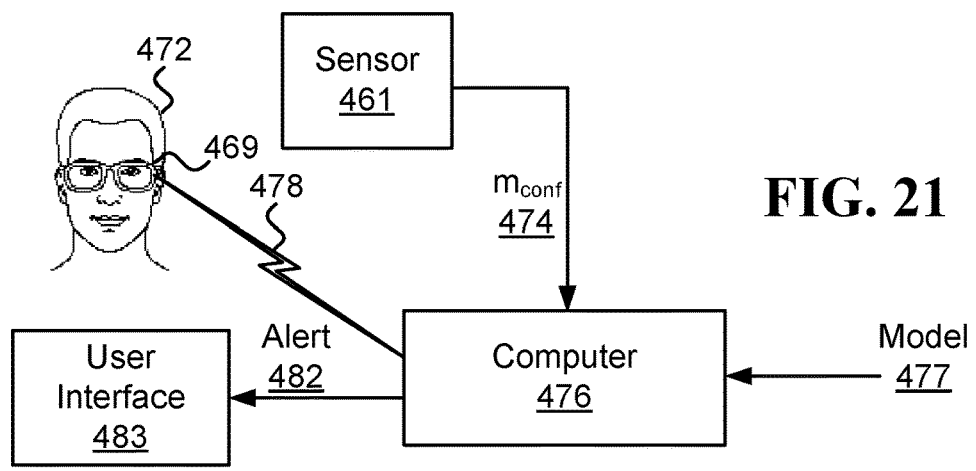
FIG. 21 illustrates an embodiment of a system that includes a user interface, which notifies a user when the stress level of the user reaches a predetermined threshold.

In one embodiment, the system further includes a user interface (UI), such as user interface 483 illustrated in FIG. 21, which notifies the user when the stress level reaches a predetermined threshold. Optionally, the UI notifies the user by an audio indication, a visual indication, and/or a haptic notification. Optionally, the greater the change to the temperature of the periorbital areas, the higher the detected stress level, and the indication is proportional to the stress level. Optionally, the UI also provides the user with encouragement not to engage in certain behavior that causes stress, such as displaying anger, screaming, denigrating others, lying, and/or cheating. In one example, the encouragement may include evidence based on detected stress levels of the user, which indicates that conducting in the certain behavior increases stress. In another example, the encouragement may include reminding the user that the certain behavior is against the user's beliefs and/or the certain behavior is contrary to the user's goals, interests, and/or resolutions.

In one embodiment, a system configured to alert about stress includes at least CAM1 and CAM2 located at least 0.5 cm to the right and to the left of the vertical symmetry axis that divides the user's face, respectively. CAM1 and CAM2 take thermal measurements of regions on the periorbital areas of the right and left eyes ($TH_{ROI1}$ and $TH_{ROI2}$, respectively) of the user. UI 483 provides an alert about a stress level reaching a threshold. Optionally, the system includes a frame that is worn on the user's head, CAM1 and CAM2 are physically coupled to the frame, weighs below 10 g each, and located less than 15 cm from the user's face. Optionally, the system includes a transmitter that may be used to transmit $TH_{ROI1}$ and $TH_{ROI2}$ to a computer that detects the stress level based on $TH_{ROI1}$ and $TH_{ROI2}$. Optionally, responsive to detecting a stress level that reaches a threshold, the computer commands the user interface to provide the alert. For example, the computer may send a signal to a smartphone app, and/or to a software agent that has control of the user interface, to provide the alert.

One embodiment of a method for alerting about stress includes at least the following steps: In Step 1, taking thermal measurements of regions on the periorbital areas of the right and left eyes ($TH_{ROI1}$ and $TH_{ROI2}$, respectively) of a user utilizing first and second CAMs worn on the user's head and located at least 0.5 cm to the right and to the left of the vertical symmetry axis that divides the user's face, respectively. And in Step 2, alerting about a stress level that is detected based on $TH_{ROI1}$ and $TH_{ROI2}$. Optionally, the alert about the allergic reaction is provided as text, image, sound, and/or haptic feedback.

Optionally, the method further includes generating feature values based on $TH_{ROI1}$ and $TH_{ROI2}$, and using a model for detecting the stress level based on the feature values. The model was trained based on previous $TH_{ROI1}$ and $TH_{ROI2}$ of the user, taken during different days, which include: a first set of measurements taken while the user had a first stress level according to a predetermined stress scale, and a second set of measurements taken while the user had a second stress level according to the predetermined stress scale.

Optionally, the method further includes generating feature values based on $TH_{ROI1}$ and $TH_{ROI2}$, and using a model for detecting the stress level based on the feature values. The model was trained based on previous $TH_{ROI1}$ and $TH_{ROI2}$ of one or more users, taken during different days, which comprise: a first set of measurements taken while the one or more users had a first stress level according to a predetermined stress scale, and a second set of measurements taken while the one or more users had a second stress level according to the predetermined stress scale.

The above steps of generating the feature values and utilizing the model may be performed multiple times throughout the period of the different days during which $TH_{ROI1}$ and $TH_{ROI2}$ were taken, each time utilizing a subset of $TH_{ROI1}$ and $TH_{ROI2}$ taken during a different window of a certain length. In these embodiments, the alerting in Step 2 may be done at a certain time for which a certain stress level is detected (which warrants an alert).

Figure 18:
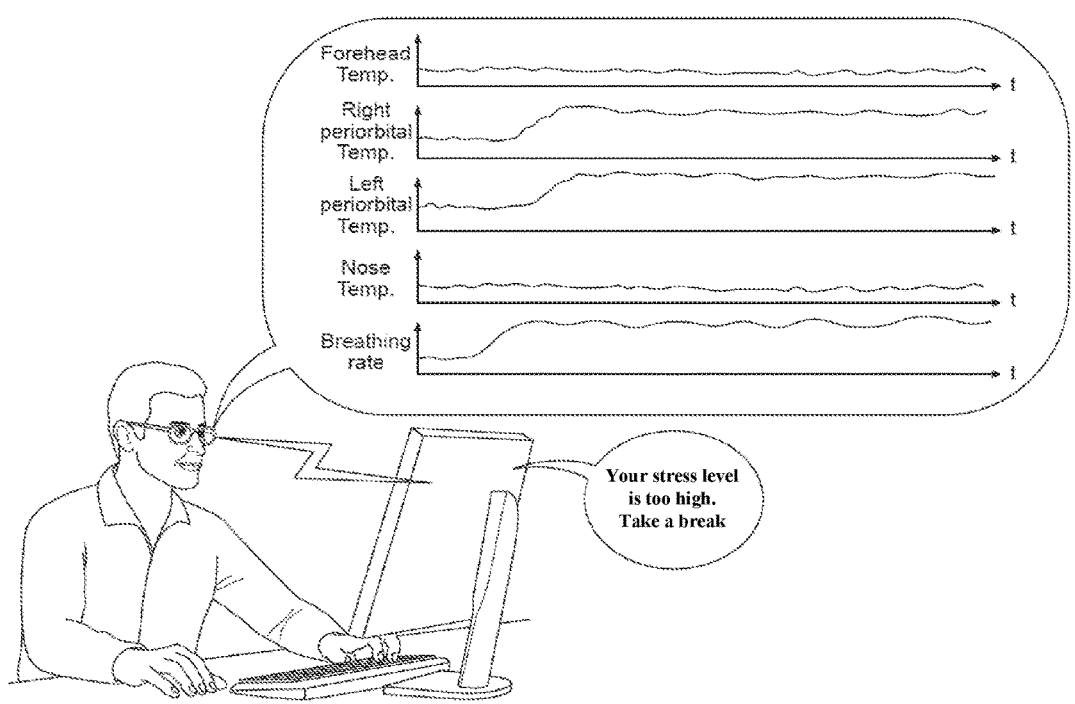
FIG. 18 illustrates a scenario in which a system suggests to the user to take a break in order to reduce the stress level.

FIG. 18 illustrates a scenario in which a system (which measures the forehead, right and left periorbital areas, nose, and below the nostrils) suggests to the user to take a break in order to reduce the stress level of the user. The system may suggest the user to partake in at least one of the following activities when the stress level reaches a first threshold: practice pranayama, physical exercise, listen to brainwave entrainment, and listen to positive loving statements. Optionally, the computer suggests to the user to stop the activity when the stress level gets below a second threshold. Optionally, the system shows the user video comprising objects, and the detected stress level associated with the objects.

Figure 20:
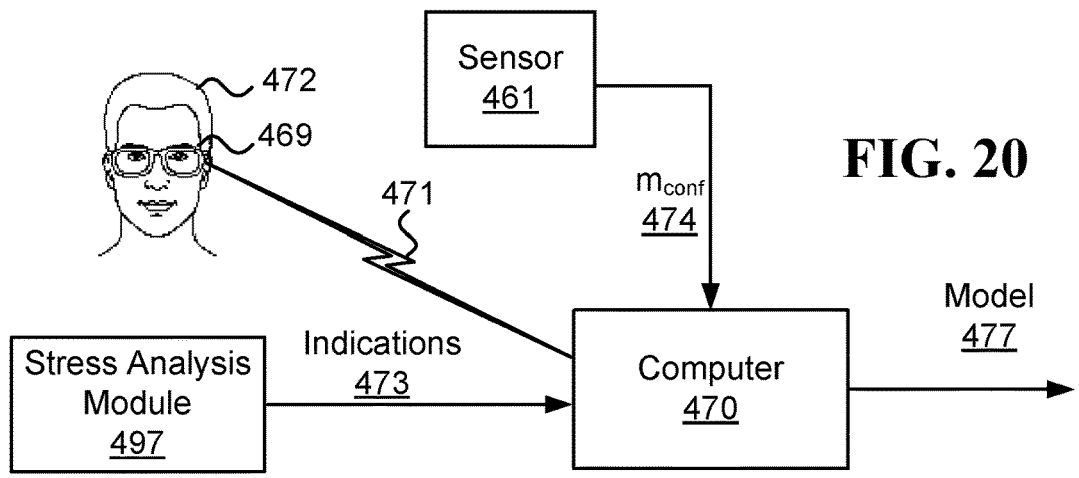
FIG. 20 illustrates an embodiment of a system that generates a personalized model to detect stress based on thermal measurements of the face.

FIG. 20 illustrates one embodiment of a system configured to generate a personalized model for detecting stress based on thermal measurements of the face. The system includes a frame, first and second CAMs, and a computer 470. The first and second CAMs take thermal measurements 471 of regions on the periorbital areas of the right and left eyes ($TH_{ROI1}$ and $TH_{ROI2}$, respectively) of the user 472.

The computer 470 generates samples based on data comprising: (i) $TH_{ROI1}$ and $TH_{ROI2}$ 471, and (ii) indications 473 corresponding to different times, which are indicative of stress levels of the user at the different times. Optionally, each sample comprises: (i) feature values generated values based on $TH_{ROI1}$ and $TH_{ROI2}$ taken during a certain period, and (ii) a label indicative of a stress level of the user during the certain period. Optionally, at least one of the feature values in a sample may be generated based on other sources of information such as physiological measurements of the user 472 and/or measurements of the environment in which the user 472 was in when while $TH_{ROI1}$ and $TH_{ROI2}$ 471 were taken. Optionally, the stress levels indicated in the indications 473 correspond to levels of a known stress level scale. The computer 470 trains a model 477 based on the samples. Optionally, the computer 470 also provides the model 477 to be used by a system that detects stress based on $TH_{ROI1}$ and $TH_{ROI2}$.

The indications 473 may be generated in different ways, in different embodiments. One or more of the indications 473 may be (i) generated by an entity that observes the user 472, such as a human observer or a software program (e.g., a software agent operating on behalf of the user 472), (ii) provided by the user 472, such as via a smartphone app by pressing a certain button on a screen of a smartphone, and/or by speech that is interpreted by a software agent and/or a program with speech analysis capabilities, (iii) determined based on analysis of behavior of the user 472, such as by analyzing measurements of a camera and/or a microphone that indicate that the user 472 is experiencing a certain stress level, and (iv) determined based on physiological signals of the user 472 that are not thermal measurements of one or more ROIs on the face, such as measurements of the user's heart rate and/or brainwave activity.

Optional stress analysis module 497 receives descriptions of events corresponding to when at least some of $TH_{ROI1}$ and $TH_{ROI2}$ 471 were taken, and generates one or more of the indications 473 based on analyzing the descriptions. The stress analysis module 497 is implemented by the computer 470 or another computer. Optionally, all of the indications 473 are generated by the stress analysis module 497. Optionally, the stress analysis module 497 may be a module of a software agent operating on behalf of the user 472. The descriptions received by the stress analysis module 497 may include various forms of information. In one example, the descriptions include content of a communication of the user 472, and the stress analysis module 497 utilizes semantic analysis in order to determine whether the communication is indicative a stressful event for the user 472 (e.g., the communication is indicative of something going wrong at work). Optionally, the stress analysis module 497 utilizes a machine learning-based model to calculate based on features derived from the communication, a predicted stress level for the user 472. In another example, the stress analysis module 497 receives images of an event, such as images taken by an outward-facing head-mounted visible-light camera, utilizes image analysis to determine whether the event corresponds to a stressful event, and utilizes a machine learning-based model to calculate the predicted stress based on features derived from the images.

The model is trained on samples comprising feature values based on $TH_{ROI1}$ and $TH_{ROI2}$, and additional feature values described in the following examples:

In a first example, the additional feature values include additional thermal measurements, taken with another CAM, of an ROI that includes the nasal and/or mouth regions.

In a second example, the additional feature values are indicative of one or more of the following signals of the user 472: a heart rate, heart rate variability, brainwave activity, galvanic skin response, muscle activity, and an extent of movement.

In a third example, the additional feature values are measurements ($m_{conf}$ 474) of the user 472 and/or of the environment in which the user 472 was in while $TH_{ROI1}$ and $TH_{ROI2}$ 471 were taken. Optionally, $m_{conf}$ 474 are taken by a sensor 461, which may be physically coupled to the frame. In another example, the sensor 461 is coupled to a device carried by the user, such as a smartphone, a smartwatch, and/or smart clothing (e.g., clothing embedded with sensors that can measure the user and/or the environment). In yet another example, the sensor 461 may be an external sensor that is not carried by the user. Optionally, the computer 470 is generates, based on $m_{conf}$ 474, one or more feature values of at least some of the samples. $m_{conf}$ 474 are indicative of an extent to which one or more confounding factors occurred while $TH_{ROI1}$ and $TH_{ROI2}$ 471 were taken.

In one embodiment, the sensor 461 is a visible-light camera physically coupled to the frame, which takes images of a region on the face of the user 472, which includes at least 25% of the $ROI_1$ and/or $ROI_2$. Optionally, the confounding factor in this embodiment involves inflammation of the skin, skin blemishes, food residues on the face, talking, eating, drinking, and/or touching the face. In another embodiment, the sensor 461 includes a movement sensor that measures a movement of the user 472. Optionally, the confounding factor in this embodiment involves the user 472 walking, running, exercising, bending over, and/or getting up from a sitting or lying position. In yet another embodiment, the sensor 461 measures at least one of the following environmental parameters: a temperature of the environment, a humidity level of the environment, a noise level of the environment, air quality in the environment, a wind speed in the environment, an extent of precipitation in the environment, and an infrared radiation level in the environment.

In some embodiments, the samples used to train the model 477 include samples that were generated based on $TH_{ROI1}$ and $TH_{ROI2}$ of the user 472 taken while the user 472 had different stress levels. In one embodiment, one or more samples that were generated based on $TH_{ROI1}$ and $TH_{ROI2}$ of the user 472 taken while a stress level of the user 472 reached a threshold. Optionally, the stress level is evaluated using one or more known stress level scales. Optionally, a user whose stress level reaches the threshold is considered "stressed". Additionally, in this embodiment, the samples include one or more samples that were generated based $TH_{ROI1}$ and $TH_{ROI2}$ of the user 472, which were taken while a stress level of the user 472 did not reach the threshold. Optionally, a user whose stress level does not reach the threshold is not considered "stressed". Thus, the samples may be utilized to train a model that can help distinguish between cases in which $TH_{ROI1}$ and $TH_{ROI2}$ of the user 472 are taken while the user 472 is stressed (and/or the user 472 has a certain stress level), and cases in which $TH_{ROI1}$ and $TH_{ROI2}$ of the user 472 are taken while the user 472 is not stressed (and/or the user 472 does not have a certain stress level).

The samples used to train the model 477 may include samples generated based on measurements taken while user 472 was in different environments. In one example, the samples comprise first and second samples that are based on $TH_{ROI1}$ and $TH_{ROI2}$ of the user 472 taken during first and second periods, respectively. Optionally, different environmental conditions prevailed during the first and second periods, which involved one or more of the following differences: (i) the temperature of the environment in which the user 472 was during the first period was at least 10° C. higher than the temperature of the environment in which the user 472 was during the second period; (ii) the humidity level in the environment in which the user 472 was during the first period was at least 30% higher than the humidity level in the environment in which the user 472 was during the second period; and (iii) the user 472 was exposed to rain, hail, and/or snow during the first period and the user was not exposed to any of rain, hail, and snow during the second period.

Additionally or alternatively, the samples utilized to train the model 477 may include samples generated based on measurements taken while the user 472 was in various situations. In one example, the samples comprise first and second samples that are based on $TH_{ROI1}$ and $TH_{ROI2}$ of the user 472 taken during first and second periods, respectively. Optionally, the user 472 was in different situations during the first and second periods, which involved one or more of the following differences: (i) the user 472 was sedentary during the first period, while the user 472 was walking, running, and/or biking during the second period; and (ii) the user 472 was indoors during the first period, while the user 472 was outdoors during the second.

Additionally or alternatively, the samples utilized to train the model 477 may be based on $TH_{ROI1}$ and $TH_{ROI2}$ taken during different days and/or over a long period, such as more than a week, more than a month, or more than a year.

Training the model 477 may involve one or more of the various computational approaches mentioned in this disclosure for training a model used to detect a physiological response. In one example, training the model 477 may involve selecting, based on the samples, a threshold; if a certain feature value reaches the threshold then a certain level of stress of the user is detected. In another example, the computer 470 utilizes a machine learning-based training algorithm to train the model 477 based on the samples. Optionally, the model comprises parameters of at least one of the following models: a regression model, a model utilized by a neural network, a nearest neighbor model, a model for a support vector machine for regression, and a model of a decision tree.

In some embodiments, the computer 470 may utilize deep learning algorithms to train the model 477. In one example, the model 477 may include parameters describing multiple hidden layers of a neural network. In one embodiment, when $TH_{ROI1}$ and $TH_{ROI2}$ include measurements of multiple pixels, such as when CAM includes a FPA, the model 477 may include parameters of a convolution neural network (CNN). In one example, a CNN may be utilized to identify certain patterns in the thermal images, such as patterns of temperatures on the forehead that may be indicative of a certain physiological response (e.g., a headache, stress, or anger). In another embodiment, detecting the stress level may be done based on multiple, possibly successive, measurements. For example, stress may involve a progression of a state of the user (e.g., a gradual warming of certain areas of the forehead). In such cases, detecting the stress level may involve retaining state information that is based on previous measurements. Optionally, the model 477 may include parameters that describe an architecture that supports such a capability. In one example, the model 477 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In one embodiment, training the model 477 involves altering parameters of another model, which is generated based on $TH_{ROI1}$ and $TH_{ROI2}$ of one or more other users. For example, the computer 470 may utilize the other model as an initial model. As the samples are acquired from measurements of the user 472, the computer 470 may update parameters of the initial model based on the samples. Thus, this process may be considered personalizing a general model according to measurements of the user 472.

Once the model 477 is generated, it may be utilized to detect stress of the user 472 based on other $TH_{ROI1}$ and $TH_{ROI2}$ of the user 472, which are not among $TH_{ROI1}$ and $TH_{ROI2}$ 471 that were used for training the model 477. Such utilization of the model 477 is illustrated in FIG. 21, which illustrates one embodiment of a system configured to perform personalized detection of stress based on thermal measurements of the periorbital area. One embodiment of the illustrated system includes a frame 469, first and second CAMs, and a computer 476.

The computer 476 is configured to: generate feature values based on $TH_{ROI1}$ and $TH_{ROI2}$ 478 and utilize the model 477 to detect the stress level of the user 472 based on the feature values. Optionally, the model 477 was trained based on previous $TH_{ROI1}$ and $TH_{ROI2}$ of the user 472 (e.g., $TH_{ROI1}$ and $TH_{ROI2}$ 471), which were taken during different days. The feature values generated based on $TH_{ROI1}$ and $TH_{ROI2}$ 478 are similar in their nature to the feature values generated based on $TH_{ROI1}$ and $TH_{ROI2}$ 471, which were discussed in more detail above. Optionally, the computer 476 and the computer 470 may utilize the same modules and/or procedures to generate feature values based on $TH_{ROI1}$ and $TH_{ROI2}$ (and possibly other data). Optionally, the computer 476 receives measurements $m_{conf}$ 474 indicative of an extent to which a confounding factor occurred while $TH_{ROI1}$ and $TH_{ROI2}$ 478 were taken, as discussed above.

Since the model 477 is personalized for the user 472, when such a model is trained for different users, it may lead to different detections of stress, even when provided with similar $TH_{ROI1}$ and $TH_{ROI2}$ of the users. In one example, first and second models are generated based on previous $TH_{ROI1}$ and $TH_{ROI2}$ of first and second different users, respectively. Responsive to utilizing the first model, a first value is detected based on first feature values generated based on $TH_{ROI1}$ and $TH_{ROI2}$ of the first user, which is indicative of a first stress level. Responsive to utilizing the second model, a second value is detected based on second feature values generated based on $TH_{ROI1}$ and $TH_{ROI2}$ of the second user, which is indicative of a second stress level. In this example, $TH_{ROI1}$ and $TH_{ROI2}$ of the first user indicate a greater temperature change at the periorbital areas of the first user compared to the change at the periorbital areas of the second user indicated by $TH_{ROI1}$ and $TH_{ROI2}$ of the second user. However, in this example, the first stress level is lower than the second stress level.

Some aspects of this disclosure involve monitoring a user over time with CAM that takes thermal measurements of a region on a periorbital area ($TH_{ROI1}$) of the user. One application for which $TH_{ROI1}$ may be useful is to detect the stress level of the user. Analysis of these detections combined with information regarding factors that affected the user at different times, which may be considered potential stressors, can reveal which of the factors may be stressor that increase the stress level of the user.

Some examples of factors that may be considered potential stressors for certain users include being in certain locations, interacting with certain entities, partaking in certain activities, or being exposed to certain content. Having knowledge of which potential stressor are likely to actually be stressors for a certain user can help that user avoid the stressors and/or take early measures to alleviate the effects of the stress they cause.

Figure 22:
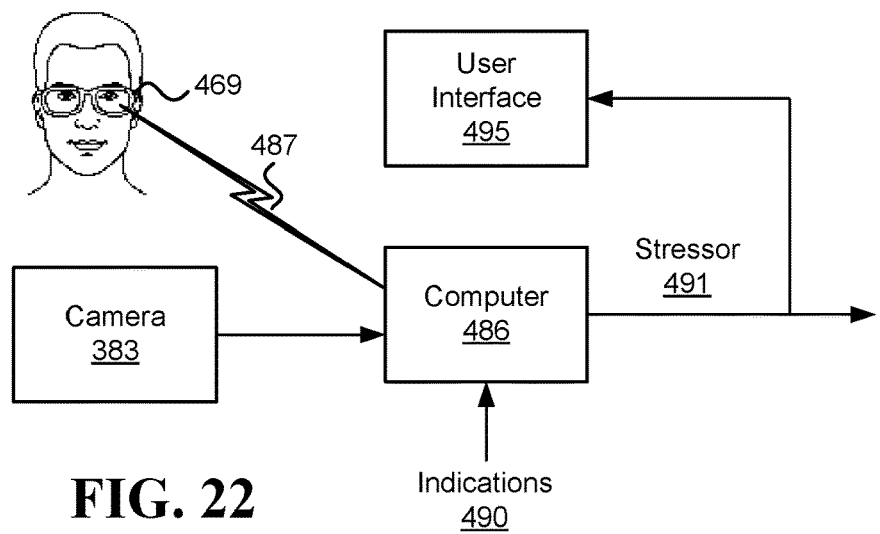
FIG. 22 illustrates an embodiment of a system that selects a stressor.

FIG. 22 illustrates one embodiment of a system configured to select a stressor. The system includes at least a computer 486 and CAM. The system may optionally include a frame 469, a camera 383, and/or a UI 495. In one example, CAM takes thermal measurements of the periorbital area of the right eye, and an additional CAM (CAM2) takes thermal measurements of a region on the periorbital area of the left eye ($TH_{ROI2}$) of the user.

In one embodiment, computer 486 calculates, based on the thermal measurements 487 (e.g., $TH_{ROI1}$ and $TH_{ROI2}$), values that are indicative of stress levels of the user at different times (i.e., detect the stress levels of the user at the different times). Optionally, $TH_{ROI1}$ and $TH_{ROI2}$ include thermal measurements taken while the user had at least two different stress levels according to a predetermined stress scale. Optionally, the thermal measurements 487 comprise thermal measurements taken during different days.

In some embodiments, the system that selects a stressor may include additional CAMs that take thermal measurements of one or more regions on the user's forehead, nose, and/or below the nostrils. Optionally, thermal measurements taken by the additional CAMs are utilized by the computer 486 when calculating the user's stress level.

Furthermore, the computer 486 may receive indications 490 of factors that affected the user at various times, which may be considered potential stressors. The computer 486 also selects a stressor 491, from among the potential stressors, based on the indications 490 and the values that are indicative of stress levels of the user at different times. Optionally, each of the indications 490 is indicative of a time during which the user was exposed to a potential stressor. Additionally or alternatively, each of the indications 490 may be indicative of a time during which the user was affected by a potential stressor. In some embodiments, at any given time, the user may be exposed to more than one of the potential stressors. Thus, in some embodiments, at least some of the thermal measurements 487, and optionally all of the thermal measurements 487, were taken while the user was exposed to two or more potential stressors.

In one embodiment, the indications 490 include a list of periods of time during which various potential stressors affected the user. Optionally, the indications 490 are provided via a data structure and/or a queryable system that provides information for different points in time about which of the potential stressors affected the user at the points in time. There are various types of potential stressors that may be indicated by the indications 490.

In one embodiment, one or more of the potential stressors may relate to various locations the user was at (e.g., work, school, doctor's office, in-laws house, etc.) and/or to various activities the user partakes in (e.g., driving, public speaking, operating machinery, caring for children, choosing clothes to wear, etc.)

In another embodiment, one or more of the potential stressors may relate to entities with which the user interacts. For example, an entity may be a certain person, a person with a certain role (e.g., a teacher, a police officer, a doctor, etc.), a certain software agent, and/or an avatar (representing a person or a software agent).

In yet another embodiment, one or more of the potential stressors may relate to situations in which the user is in, which can increase stress. For example, a situation may be being unemployed, having financial difficulties, being separated after being in a relationship with another person, being alone, or awaiting an important event (e.g., an exam, a job interview, or results of an important medical test). In another example, a situation may relate to a physical condition of the user, such as being sick or suffering from a certain chronic disease. Optionally, when the situations described above are applicable to another person who the user cares about (e.g., a spouse, child, parent, or close friend), then those situations, which relate to the other person, may be considered potential stressors that can lead to stress in the user.

In still another embodiment, one or more of the potential stressors may relate to the user's behavior. For example, behaving in a way that is argumentative, manipulative, deceptive, and/or untruthful may increase the stress level.

When a user is affected by one or more potential stressors, in some embodiments, the stress level of the user may depend on quantitative aspects of the potential stressors. In some examples, the degree to which a potential stressor affects the user's stress level may depend on the amount of time the potential stressor affected the user (e.g., the duration the user spent at a certain location) and/or the magnitude of the potential stressor (e.g., the extent to which an argument was heated—which may be expressed by the level of noise in peoples shouting). In some embodiments, the indications 490 include values that quantify how much at least some of the potential stressors affected the user.

The stressor 491 is a potential stressor that is correlated with an increase in the stress level of the user. Additionally, in some embodiments, the stressor 491 may be a potential stressor that may be considered a direct cause of the increase in the stress level of the user. When considering how being affected by the potential stressors relates to the stress level of the user, an effect of the stressor 491 is higher than effects of most of the potential stressors.

The effect of a potential stressor may be considered a measure of how much the potential stressor influences the stress level the user. This can range from no influence to a profound influence. More specifically, in one embodiment, the effect of a potential stressor is a value indicative of the average extent of change to the stress level of the user at a time $t+\Delta$ after being affected by the potential stressor at time t. Here, $\Delta$ corresponds to the typical time it may take the stress to manifest itself in the user after being affected by the potential stressor. This time may range from a short period e.g., several seconds or minutes, to hours.

There are various ways in which the computer 486 may select, based on the indications 490 and the thermal measurements 487, the stressor 491 from among the potential stressors being considered.

In some embodiments, the computer 486 performs a direct analysis of the effect of each of the potential stressors in order to identify which ones have a large effect on the user. Optionally, the effect of each potential stressor is indicative of the extent to which it increases the stress level of the user. Optionally, the effect of each potential stressor is calculated by determining, based on the indications 490, times at which the user was affected by the potential stressor, and observing the stress level of the user at one or more times that are up to a certain period $\Delta$ later (where $\Delta$ depends on the user and the type of stressor). In one example, $\Delta$ is ten seconds, thirty seconds, or one minute. In another example, $\Delta$ is one minute, ten minutes, or one hour.

In one embodiment, a stress level (or change to the stress level) following being affected by a potential stressor is the maximum stress level that is detected from the time t the user was affected by the potential stressor until the time $t+\Delta$. In another example, the stress level (or change to the stress level) following being affected by the potential stressor is the extent of the stress level and/or change to the stress level that is detected at a time $t+\Delta$ (when the user was affected by the potential stressor at time t). Optionally, the extent may be normalized based on a quantitative value representing how much the user was affected by the potential stressor. Optionally, the stress level may be normalized with respect to a stress level detected prior to being affected by the potential stressor.

Following a calculation of the effects of the potential stressors, in one embodiment, the computer 486 selects the stressor 491 from among the potential stressors. Optionally, the stressor 491 is a potential stressor that has a maximal effect (i.e., there is no other potential stressor that has a higher effect). Optionally, the stressor 491 is a potential stressor that has an effect that reaches a threshold, while the effects of most of the potential stressors do not reach the threshold.

In one embodiment, in order to increase confidence in the selection of the stressor, the stressor 491 is selected based on at least a certain number of times in which the user was affected by the stressor 491. For example, the certain number may be at least 3 or 10 different times. Thus, in this embodiment, potential stressors that did not affect the user at least the certain number of times are not selected.

In some embodiments, the computer 486 generates a machine learning-based model based on the indications 490 and the values indicative of the stress levels of the user, and selects the stressor 491 based on an analysis of the model. Optionally, the computer 486 generates samples used to train the model. The samples used to train the model may correspond to different times, with each sample corresponding to a time $t+\Delta$ including feature values and a label indicative of the stress level of the user at the time $t+\Delta$. Each sample may be considered to represent a snapshot of potential stressors that affected the user during a certain period, and a label that is indicative of the stress level of the user following being affected by those potential stressors. Given multiple such samples, a machine learning training algorithm can be utilized to train a model for a predictor module that can predict the stress level at a certain time based on feature values that describe potential stressors that affected the user during a certain period of time leading up to the certain time. For example, if the model is a regression model, the predictor module may perform a dot product multiplication between a vector of regression coefficients (from the model) and a vector of the feature values in order to calculate a value corresponding to the predicted stress level of the user at the certain time.

When such a predictor module is capable of predicting stress level of the user based on the feature values described above, this may mean that the model captures, at least to some extent, the effects of at least some of the potential stressors on the stress level of the user.

Training the model based on the samples described above may involve utilizing one or more of various training algorithms. Some examples of models that may be generated in order to be utilized by the predictor module described above include the following models: a regression model (e.g., a regression model), a naïve Bayes model, a Bayes network, a support vector machine for regression, a decision tree, and a neural network model, to name a few possibilities. There are various training algorithms known in the art for generating these models and other models with similar properties.

The predictor module may be provided multiple inputs representing the potential stressors that affected the user at different points of time, and have a capability to store state information of previous inputs corresponding to earlier times when it comes to predict the stress level of the user at a certain time. For example, the predictor module may be based on a recurrent neural network.

Once the model is trained, in some embodiments, it is analyzed by the computer 486 in order to determine the effects of one or more of the stressors on the stress level of the user. Depending on the type of model that was trained, this analysis may be performed in different ways.

In one embodiment, the computer 486 performs the analysis of the model by evaluating parameters of the model that correspond to the potential stressors. Optionally, the computer 486 selects as the stressor 491 a certain potential stressor that has a corresponding parameter that is indicative of an effect that reaches a threshold while effects indicated in parameters corresponding to most of the stressors do not reach the threshold. In one example, the model may be a linear regression model in which each potential stressor corresponds to a regression variable. In this example, a magnitude of a value of a regression coefficient may be indicative of the extent of the effect of its corresponding potential stressor. In another example, the model may be a naïve Bayes model in which various classes correspond to stress levels (e.g., a binary classification model that is used to classify a vector of feature values to classes corresponding to "stressed" vs. "not stressed"). In this example, each feature value may correspond to a potential stressor, and the class conditional probabilities in the model are indicative of the effect of each of the potential stressors on the user.

In another embodiment, the computer 486 performs an analysis of the model, which may be characterized as "black box" analysis. In this approach, the predictor module is provided with various inputs that correspond to different potential stressors that affect the user, and calculates, based on the inputs and the model, various predicted stress levels of the user. The various inputs can be used to independently and/or individually increase the extent to which each of the potential stressors affects the user. This type of the model probing can help identify certain potential stressors that display an increase in the predicted stress level, which corresponds to an increase in the extent to which the potential stressors affect the user (according to the model). Optionally, the stressor 491 is a potential stressor for which a positive correlation is observed between increasing the extent to which the potential stressor affects that user, and the predicted stress level of the user. Optionally, the stressor 491 is selected from among the potential stressors, responsive to identifying that: (i) based on a first subset of the various predicted stress levels of the user, an effect of the stressor 491 reaches a threshold, and (ii) based on a second subset of the various predicted stress levels of the user, effects of most of the potential stressors do not reach the threshold.

The indications 490 may be received from various sources. In one embodiment, the user may provide at least some of the indications 490 (e.g., by inputting data via an app and/or providing vocal annotations that are interpreted by a speech analysis software). In other embodiments, at least some of the indications 490 are provided by analysis of one or more sources of data. Optionally, the computer 486 generates one or more of the indications 490 based on an analysis of data obtained from the one or more sources. The following four examples, discussed herein in relation to allergy, are also relevant as examples of sources of data that may be utilized to identify potential stressors that affected the user at different times: (i) a camera 383 captures images of the surroundings of the user, (ii) sensors such as microphones, accelerometers, thermometers, pressure sensors, and/or barometers may be used to identify potential stressors by identifying what the user is doing and/or under what conditions, (iii) measurements of the environment that user is in, and (iv) IoT devices, communications of the user, calendar, and/or billing information may provide information that may be used in some embodiments to identify potential stressors.

Knowledge of the stressor 491 may be utilized for various purposes. Optionally, the knowledge of the stressor 491 is utilized by a software agent operating on behalf of the user in order to better serve the user. In some embodiments, information about the stressor 491 is provided to the user via a UI 495, such as a smartphone, HMD, and/or an earphone).

UI 495 may be utilized on a day-to-day basis to warn the user when the stressor 491 is detected. For example, the computer 486 may provide real-time indications of potential stressors. Upon detecting that those potential stressors include the stressor 491, the UI notifies the user about the stressor in order for the user to take action, such as reducing exposure to the stressor (e.g., by leaving a certain location or ceasing a certain activity) and/or performing actions aimed at reducing stress (e.g., a breathing exercises).

In one embodiment, a software agent identifies that the user is going to be affected by the stressor 491 (e.g., by analyzing the user's calendar schedule and/or communications), and suggests the user, via UI 495, to perform various exercises (e.g., breathing exercises) and/or prepare himself for the stressor 491 in order to reduce its effect.

With little modifications, the system illustrated in FIG. 22 may be utilized to detect a calming factor that reduces the user's stress, rather than one that increases it. In particular, instead of selecting a stressor that has a large effect (or maximal effect) on the user, a factor that has a large negative effect on the stress level may be selected. Optionally, in the event that a high stress level of the user is detected, the calming factor may be suggested to the user (to reduce the user's stress level).

The following is a description of steps involved in one embodiment of a method for selecting a stressor. The steps described below may be used by systems modeled according to FIG. 22, and may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method. In one embodiment, the method for alerting about stress includes at least the following steps:

In Step 1, taking, utilizing a CAM, thermal measurements of a region on a periorbital area ($TH_{ROI1}$) of a user who wears CAM. Optionally, the region on the periorbital area is a region of the periorbital area of the right eye, and this step also involves taking, utilizing a second inward-facing head-mounted thermal camera (CAM2), thermal measurements of a region on the periorbital area of the left eye ($TH_{ROI2}$).

In Step 2, detecting extents of stress based on $TH_{ROI1}$. Optionally, detecting the extents may be done utilizing the computer, as discussed above. Optionally, the extents are also detected based on $TH_{ROI2}$ (and/or other thermal measurements mentioned below).

In Step 3, receiving indications of times during which the user was exposed to potential stressors.

And in Step 4, selecting the stressor, from among the potential stressors, based on the indications and the extents. Optionally, during most of the time the user was affected by the stressor, an effect of the stressor, as manifested via changes to $TH_{ROI1}$, was higher than effects of most of the potential stressors.

In one embodiment, the method may optionally include a step of taking images of the surroundings of the user and generating at least some of the indications based on analysis of the images. Optionally, the images are taken with the camera 383, as discussed above.

In one embodiment, selecting the stressor is done by generating a machine learning-based model based on the indications and extents, and selecting the stressor based on an analysis of the model. In one example, performing the analysis of the model involves evaluating parameters of the model that correspond to the potential stressors. In this example, a certain potential stressor is selected as a stress. The certain potential stressor has a corresponding parameter in the model that is indicative of an effect that reaches a threshold, while effects indicated in parameters corresponding to most of the other potential stressors do not reach the threshold. In another example, performing the analysis of the model involves: (i) providing a predictor module with various inputs that correspond to different potential stressors that affect the user; (ii) calculating, based on the inputs and the model, various predicted stress levels; (iii) determining, based on the various predicted stress levels, effects of the potential stressors; and (iv) selecting the stressor based on the effects. In this example, the effect of the stressor reaches a threshold, while effects of most of the other potential stressors do not reach the threshold.

In one embodiment, a system configured to detect an irregular physiological response of a user while the user is exposed to sensitive data includes at least a head-mounted display (HMD), a CAM, and a computer. Optionally, CAM is coupled to the HMD (e.g., they are both components of an HMS). The HMD exposes sensitive data to a user who wears the HMD. For example, the HMD may display text, images, and/or video. Optionally, the HMD may be a virtual reality display or an augmented reality display. Optionally, the HMD is designed such that only the user who wears the HMD can view the sensitive data displayed on the HMD. CAM takes thermal measurements of an ROI ($TH_{ROI}$) on the user's face while the user is exposed to the sensitive data, and is optionally located less than 15 cm from the face. In some embodiments, the system may include additional CAMs that take thermal measurements of additional ROIs on the user's face. In some embodiments, CAM may weigh below 5 g and/or CAM may be located less than 5 cm from the user's face.

The computer detects, based on certain $TH_{ROI}$ taken while the user is exposed to certain sensitive data, whether the user experienced the irregular physiological response while being exposed to the certain sensitive data.

In one embodiment, the certain $TH_{ROI}$ are taken during a certain window of time that depends on the type of the irregular physiological response (e.g., a certain stress level and/or a certain emotional response). Optionally, the window is at least five seconds long, at least thirty seconds long, at least two minutes long, at least five minutes long, at least fifteen minutes long, at least one hour long, or is some other window that is longer than one second. Optionally, during the time the user is exposed to sensitive data, $TH_{ROI}$ from multiple windows may be evaluated (e.g., using a sliding window approach), which include a window that contains a period during which the certain $TH_{ROI}$ were taken.

In some embodiments, detecting the irregular physiological response is done based on additional inputs such as thermal measurements taken by additional CAMs (which may cover additional ROIs), and/or values of physiological signals and/or behavioral cues of the user such as heart rate, breathing rate, galvanic skin response, movements, facial expressions, and/or brainwave activity. Optionally, the values of physiological signals and/or behavioral cues are obtained utilizing sensors other than CAMs.

What corresponds to an "irregular physiological response" may vary between different embodiments. The following are some examples of criteria and/or ways of determining whether a physiological response is considered an "irregular physiological response". In one example, the irregular physiological response involves the user experiencing stress that reaches a certain threshold. Optionally, for most of the time the user wears the HMD, the stress level detected for the user does not reach the certain threshold. In another example, the irregular physiological response involves the user experiencing at least a certain level of one or more of the following emotions: anxiety, fear, and anger. Optionally, for most of the time the user wears the HMD, the extent to which the user experiences the one or more emotions does not reach the certain level. In yet another example, an irregular physiological response corresponds to atypical measurement values. For example, if a probability density function is generated based on previously taken $TH_{ROI}$ of the user, values with a low probability, such as a probability value that is lower than the probability of 97% of the previously taken $TH_{ROI}$, may be considered atypical.

In order to detect the irregular physiological response, the computer may utilize $TH_{ROI}$ in various ways, as described below. Optionally, detection of the irregular physiological response is done while taking into account various factors that may influence the user's measured physiological responses, such as the user's emotional state (e.g., whether the user is anxious, distraught, or calm), the environmental conditions (e.g., the temperature, humidity level, and/or level of oxygen in the air), and/or the type of sensitive data that the user accesses.

In one embodiment, the computer compares one or more values derived from the certain $TH_{ROI}$ to a certain threshold, and determines whether the threshold is reached (which is indicative of an occurrence of the irregular physiological response). Optionally, the threshold is determined based on previously taken $TH_{ROI}$ of the user (e.g., taken when the user had an irregular physiological response). Optionally, the threshold is determined based on baseline thermal measurements of the user, and the threshold represents a difference of a certain magnitude relative to the baseline measurements. Optionally, different thresholds may be utilized to detect different types of irregular physiological responses, to detect irregular physiological responses to different types of sensitive data, and/or to detect irregular physiological responses when the user is in certain emotional states and/or under certain environmental conditions.

In another embodiment, the computer generates feature values and utilizes a machine learning-based model to detect, based on the feature values, whether the user had an irregular physiological response. One or more of the feature values are generated based on the certain $TH_{ROI}$. Optionally, at least one of the feature values is generated based on the sensitive data, e.g., the at least one of the feature values may describe properties of the sensitive data. In one example, the model may be generated based on previous $TH_{ROI}$ of the user. In another example, the model may be generated based on previous $TH_{ROI}$ of other users.

The emotional state of the user, while accessing the certain sensitive data, may influence the user's physiological response, and thus may play a role in determining whether the user had an irregular physiological response. Similarly, the environmental conditions that prevail when the user accesses the certain sensitive data, and also the type of sensitive data being accessed, may influence the user's physiological response and thus may have a bearing on whether the user's physiological response should be considered irregular or not. Addressing these factors may be done in different ways.

In one embodiment, multiple machine learning-based models may be generated utilizing different training sets of data. For example, different models may be created to detect different types of irregular physiological responses, to detect irregular physiological responses to different types of sensitive data, and/or to detect irregular physiological responses when the user is in a certain emotional state and/or under certain environmental conditions.

In another embodiment, the feature values generated by the computer may include feature values that describe one or more of the following factors: an emotional state of the user while accessing the certain sensitive data, a condition of the environment in which the user accessed the certain sensitive data, and the type of the certain sensitive data. Thus, the factors mentioned above may be considered when the determination is made regarding whether the user experienced an irregular physiological response. In one example, the computer receives values indicative of the user's emotional state while being exposed to the certain sensitive data, and utilizes a machine learning-based model to detect whether the user experienced the irregular physiological response based on the certain $TH_{ROI}$. Optionally, in this example, the machine learning-based model was trained based on previous $TH_{ROI}$ taken while the user was in a similar emotional state. In another example, the computer is receives values indicative of the environment the user was in while being exposed to the certain sensitive data (e.g., temperature and/or humidity level), and utilizes a machine learning-based model to detect whether the user experienced the irregular physiological response based on the certain $TH_{ROI}$. Optionally, in this example, the machine learning-based model was trained based on previous $TH_{ROI}$ taken while the user was in a similar environment.

Determining what constitutes a certain type of sensitive data may be done according to various criteria. In one example, different types of sensitive data involve data with different classes of content (e.g., intelligence reports vs. billing statements). In another example, different types of sensitive data involve data with different levels of sensitivity (e.g., involve different levels of security clearance). In yet another example, different types of sensitive data come from different sources. In another example, different types of sensitive data involve different types of media (e.g., text information vs. video). In still another example, different types of sensitive data may correspond to the relationship of the sensitive data to the user (e.g., data that involves someone close to the user vs. data that involves a stranger).

The following describes how the system may utilize information about the type of sensitive data the user is exposed to in order to improve the detection of an irregular physiological response during exposure to that data. In one example, certain sensitive data is associated with a first type of sensitive data, and the computer detects the irregular physiological response when the certain $TH_{ROI}$ reach a first threshold. Optionally, the first threshold is calculated based on other $TH_{ROI}$ taken while the user was exposed to sensitive data associated with the first type of sensitive data. Additionally, the user is exposed to second certain sensitive data, which is associated with a second type of sensitive data. In this case, the computer detects the irregular physiological response when second certain $TH_{ROI}$ reach a second threshold. The second certain $TH_{ROI}$ are taken while the user is exposed to the second certain sensitive data, the second threshold is calculated based on other $TH_{ROI}$ taken while the user was exposed to sensitive data associated with the second type of sensitive data. In this example, the second threshold is different from the first threshold.

In one embodiment, the sensitive data is associated with a type of data that belongs to a set that includes at least first and second types of sensitive data. The computer utilizes $TH_{ROI}$ to generate feature values, and utilizes a model to calculate, based on the feature values, an extent of the irregular physiological response. Optionally, at least one of the feature values indicates the type of sensitive data to which the user was exposed. Optionally, the model was trained based on previous $TH_{ROI}$ of one or more users and indications of the type of sensitive data to which each of the one or more users was exposed. Optionally, the previous $TH_{ROI}$ comprise at least some measurements taken while the one or more users were exposed to the first type of sensitive data and at least some measurements taken while the one or more users were exposed to the second type of sensitive data.

Detecting the irregular physiological response may involve utilization of one or more baselines. Optionally, a baseline may be indicative of typical values for the user, such as typical thermal measurements when exposed to sensitive data, the extent to which a user is typically stressed when exposed to sensitive data, and/or the extent the user typically expresses one or more of the following emotions when exposed to sensitive data: anxiety, fear, and anger. Optionally, a baseline may correspond to the user, i.e., it may represent expected values of the user. Additionally or alternatively, a baseline may correspond to multiple users, and represent expected values of other users (e.g., a general response).

In some embodiments, a baseline may be determined based on previous thermal measurements. In one example, the previous thermal measurements comprise thermal measurements of the user. In another example, the previous thermal measurements comprise thermal measurements of other users. Optionally, the previous thermal measurements are taken while being exposed to baseline sensitive data. Optionally, the baseline sensitive data may be of the same type as the certain sensitive data. Optionally, the previous thermal measurements are taken with essentially the same system as the certain $TH_{ROI}$ (e.g., the same headset or a headset with a similar positioning of CAM).

In some embodiments, multiple baselines may be generated, corresponding to different types of sensitive data, different environmental conditions, and/or different emotional states of the user. Optionally, the multiple baselines are each generated based on corresponding thermal measurements, such as thermal measurements taken while the person being measured (e.g., the user or some other user) was exposed to a certain type of sensitive data, in a certain type of environment, and/or while in a certain emotional state.

In some cases, it may be useful to generate a baseline based on measurements taken in temporal proximity to when the user is exposed to the certain sensitive data. Comparing close events may be beneficial because the shorter the time between being exposed to baseline sensitive data and being exposed to the certain sensitive data, the smaller the effect of environmental changes and/or normal physiological changes may be. In one example, the user is exposed to the certain sensitive data immediately before and/or after being exposed to the baseline sensitive data. In another example, the user is exposed to the certain sensitive data within less than 5 minutes before and/or after being exposed to the baseline sensitive data. In still another example, the user exposed to the certain sensitive data within less than 15 minutes before or after being exposed to the baseline sensitive data.

In some embodiments, a baseline may be calculated utilizing a predictor, which receives input comprising feature values describing various values such as characteristics of user (e.g., age, gender, weight, occupation), the sensitive data, the environment in which the user is in, and/or the emotional state of the user. The predictor utilizes a machine learning-based model to calculate, based on the feature values, the baseline which may be, for example, a value of thermal measurements, a stress level, or an extent of expressing a certain emotion. Optionally, the model was trained based on measurements of the user. Optionally, the model was trained based on measurements of other users.

Baseline values may be utilized by the computer in various ways. For example, thermal measurements may be normalized with respect to a baseline in order to help identify when the thermal measurements deviate from the expected values (which may be indicative of the irregular physiological response). In another example, a threshold to which the computer compares the certain $TH_{ROI}$ may be a value that is defined relative to the baseline. In yet another example, a reference time series may be selected based on a corresponding baseline (i.e., a reference time series may correspond to an irregular physiological response that occurs when the user is in a certain baseline state). In still another example, one or more feature values utilized to detect a physiological response may be generated based on a baseline value (i.e., the baseline may be one of the inputs for detecting the physiological response).

In one embodiment, $TH_{ROI}$ express temperature at the ROI, and the baseline expresses ordinary temperature at the ROI while the user is exposed to sensitive data. In another embodiment, $TH_{ROI}$ express temperature change at the ROI, and the baseline expresses ordinary temperature changes at the ROI around the time of switching from being exposed to non-sensitive data to being exposed to sensitive data. In still another embodiment, $TH_{ROI}$ express temperature change at the ROI, and the baseline expresses ordinary temperature changes at the ROI around the time of switching from being exposed to sensitive data to being exposed to non-sensitive data.

It is noted that when the user is exposed to data over a period of time, in some embodiments, each segment of data (e.g., data watched during a certain span of a few minutes) may serve both as a baseline sensitive data and/or as the certain sensitive data.

In one embodiment, the certain sensitive data is associated with a first type of sensitive data, and the computer detects the irregular physiological response when a difference between the certain $TH_{ROI}$ and a first baseline reaches a first threshold. Optionally, the first baseline is calculated based on other $TH_{ROI}$ taken while the user was exposed to sensitive data associated with the first type of sensitive data. Additionally, the user is exposed to a second certain sensitive data that is associated with a second type of sensitive data, and the computer detects the irregular physiological response while being exposed to the second certain sensitive data when a difference between second certain $TH_{ROI}$ and a second baseline reaches a second threshold. Here, the second certain $TH_{ROI}$ are taken while the user is exposed to the second certain sensitive data, the second baseline is calculated based on other $TH_{ROI}$ taken while the user was exposed to sensitive data associated with the second type of sensitive data. In this embodiment, the second threshold is different from the first threshold. Optionally, the system estimates job burnout; the greater the differences between $TH_{ROI}$ and their associated baselines, the worse is the job burnout.

In different embodiments of the system configured to detect an irregular physiological response of a user while the user is exposed to sensitive data, the ROI may comprise different regions of the face and/or the system may involve various hardware configurations (e.g., certain types of CAMs and/or additional CAMs). Optionally, measurements taken by an additional CAM are utilized to generate one or more of the feature values utilized by the computer to detect the irregular physiological response.

In one embodiment, the ROI is on periorbital area of the user and CAM includes an uncooled thermal sensor. Optionally, the ROI is on the periorbital area of the right eye, and the system includes a second CAM that takes thermal measurements of a region on the periorbital area of the left eye. Optionally, the computer detects the irregular physiological response based on the measurements of the periorbital areas of the right and left eyes.

In another embodiment, the ROI is on the user's nose and CAM includes an uncooled thermal sensor. Optionally, the ROI is on the right side of the user's nose and the system includes a second CAM that takes thermal measurements of a region on the left side of the nose. Optionally, the computer detects the irregular physiological response based on the measurements of the regions on the left and right sides of the nose.

In yet another embodiment, the ROI is on the user's forehead. Optionally, the ROI is on the right side of the user's forehead, and the system includes a second CAM that takes thermal measurements of the left side of the user's forehead. Optionally, the computer detects the irregular physiological response based on the measurements of the regions on the left and right sides of the forehead.

Figure 23:
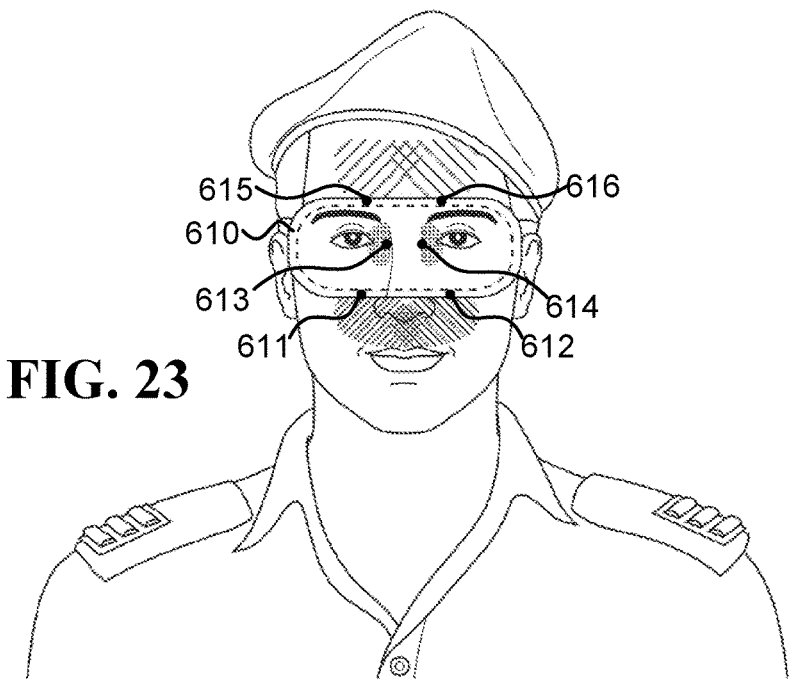
FIG. 23 illustrates an embodiment of a system that detects an irregular physiological response of a user while the user is exposed to sensitive data.

FIG. 23 illustrates one embodiment of a system configured to detect an irregular physiological response of a user while the user is exposed to sensitive data. The system includes head-mounted system HMS 610, which includes a head-mounted display (HMD) for exposing the user to sensitive data (not depicted in the figure) and six CAMs coupled to the frame of the HMS 610, which are 611 and 612 on the bottom of the frame to measure the upper lip and nose, 613 and 614 inside the HMS to measure the periorbital areas, and 615 and 616 on the top of the frame to measure the forehead (the measured regions on the face are illustrated as shaded areas). It is to be noted that though the user's eyes are visible in the figure, the front of the HMS may be opaque as is common with virtual reality headsets.

Figure 24:
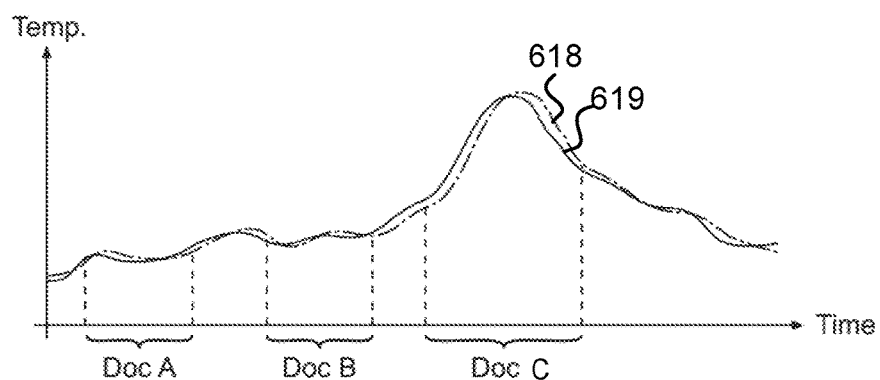
FIG. 24 illustrates detection of an irregular physiological response.

FIG. 24 illustrates detection of an irregular physiological response. The figure depicts a graph displaying temperatures at the right and left periorbital areas (lines 618 and 619 in the figure). The user is exposed to three documents via a HMD, "doc A", "doc B", and "doc C". With the first two documents ("doc A" and "doc B"), the temperatures remain low, but when the user is exposed to "doc C" the temperature rises dramatically, which in this exemplary figure may constitute an irregular physiological response.

Figure 26:
FIG. 26 illustrates triggering an alert when the user moves the HMD and touches the CAM.

In order to avoid detection of an irregular physiological response, a user exposed to sensitive data via the HMD may attempt to take evasive measures such as touching the face, moving the HMD, and/or occluding the sensors (e.g., in order to disrupt sensor measurements). An example of such behavior is illustrated in FIG. 26 in which the user moves the HMD a bit and touches a CAM, which triggers an alert.

In one embodiment, the system may detect whether the user moves the HMD relative to the face while being exposed to the certain sensitive data, based on measurements of an additional sensor (e.g., a sensor that measures a confounding factor). Optionally, the computer takes one or more security-related measures responsive to detecting that the user moved the HMD relative to the face while being exposed to the certain sensitive data. Optionally, the system identifies moving the HMD relative to the face based on one or more of the following: (i) analysis of images taken by an optical sensor physically coupled to the HMD, such as a CAM, an active near-IR camera physically coupled to the HMD, and/or a visible-light camera physically coupled to the HMD, (ii) analysis of images taken by an optical sensor that captures the user's face without being physically coupled to the HMD, such as a 2D or a 3D camera located in a position that faces the user or located on a smartwatch or a smart-shirt, and/or (iii) analysis of measurements of a non-optical sensor physically coupled to the HMD, such as a movement sensor, a miniature radar operating in the Extremely High Frequency (EHF) band, an acoustic sensor, an electroencephalogram sensor, an electromyogram sensor, a piezoelectric sensor, and/or strain gauges, as mentioned for example in the reference Li, Hao, et al. "Facial performance sensing head-mounted display" ACM Transactions on Graphics 2015, and (iv) analysis of measurements of a non-optical sensor physically coupled to the user's body, such as a movement sensor embedded in a wrist band or embedded in a smart-shirt.

It is noted that sentences such as "while being exposed to the certain sensitive data" does not include removing the HMD off the face, because after removing the HMD off the face the user is not exposed to the certain sensitive data. In one example, moving the HMD relative to the face refers to a relative movement above a minimum threshold (e.g., moving the frame to a distance that is greater than 1 cm). In another example, making facial expressions does not cause the system to detect that the user is moving the HMD relative to the face.

Some non-limiting examples of the security-related measures that the system may take include performing one or more of the following: storing in a database an indication that the user made a suspicious action (like moving the HMD relative to the face while being exposed to the certain sensitive data at a certain point in time), ceasing from exposing the user to the certain sensitive data, not allowing the user to perform a certain transaction related to the certain sensitive data, blocking the user's access to the certain sensitive data, issuing an alert, marking as suspicious the relationship between the user and the certain sensitive data, tightening the security restrictions for the user for accessing sensitive data on the system, providing the user a canary trap, and providing the user a barium meal test.

A "canary trap" refers to a practice of providing the user with a version of the sensitive data that contains certain indicators (e.g., small variations) that are unique to the version provided to the user. Thus, if the sensitive data is leaked, the user may be identified as the source based on detecting the small variations in the leaked data. A "barium meal test" refers to a practice of including in the sensitive data certain information; when the certain information reaches an entity it causes the entity to take a certain action (e.g., visit a certain website it would not ordinarily visit). Thus, detecting the certain action is indicative of the sensitive data (to which the user was exposed) being passed on to the entity.

In another embodiment, the system includes a sensor that provides measurements indicative of times at which the user touches the ROI. Optionally, touching the ROI is expected to influence $TH_{ROI}$ and/or disrupt the ability to detect the irregular physiological response. The user may touch the ROI using a finger, the palm, a tissue or a towel held by the user, a makeup-related item held by the user, a material that is expected to cool the ROI (such as a metal that is colder than the skin), and/or a material that is transparent in the visible spectrum (such as a transparent glass that is colder than the skin). Optionally, responsive to detecting that the user touched the ROI while being exposed to the certain sensitive data, the computer stores in a database an indication thereof, and/or the system may perform at least one of the aforementioned security-related measures.

In yet another embodiment, the system detects occlusion of CAM based on identifying a sudden change of more than 2° C. in $TH_{ROI}$ and/or utilizing a sensor that generates a signal indicative of whether a solid object is located between CAM and the ROI. Optionally, responsive to detecting that the user occluded CAM while being exposed to the certain sensitive data, the computer stores in a database an indication thereof and/or the system may perform at least one of the aforementioned security-related measures.

In one embodiment, the computer tightens security restrictions for the user responsive to detecting multiple occurrences possibly evasive measures such as touching the ROI, moving the HMD, and/or occluding the ROI. Optionally, the multiple occurrences are detected while the user is exposed to sensitive data that is of the same type as the certain sensitive data. Optionally, tightening security restrictions for the user involves restricting the user from performing a certain transaction related to the sensitive data. In one example, the certain transaction comprises copying, reading, and/or modifying the certain sensitive data. In another example, the certain sensitive data relates to money, and the certain transaction comprises an electronic funds transfer from one person or entity to another person or entity.

In some embodiments, responsive to a detection of the irregular physiological response, the system initiates a process to detect an illegal activity. Optionally, the process is initiated within less than two minutes after detecting the irregular physiological response. Optionally, the sensitive data belongs to an organization, the user is an employee of the organization, and the system helps in preventing illegal activities of employees related to sensitive data.

Some embodiments of the system configured to detect an irregular physiological response while being exposed to sensitive data include added security measures such as encryption of the sensitive data. Optionally, the system receives the certain sensitive data in an encrypted form, and the computer decrypts the certain sensitive data before presentation via the HMD. The decryption may involve hardware-based decryption, requesting a password from the user, and/or measuring the user with a sensor (e.g., an iris scan), and/or multi-factor authentication.

Another security measure that may be included in some embodiments of the system involves biometric identification of the user. In these embodiments, the system may include a biometric identification device, which is physically coupled to the HMD, and identifies the user while the user wears the HMD. Optionally, the computer exposes the user to the sensitive data responsive to receiving an indication that confirms the user's identity. Optionally, the biometric identification device performs one or more of the following operations: an iris scan, detection of brainwave patterns, detection of a cardiac activity pattern, and detection of thermal patterns on the user's face. Optionally, the biometric identification device performs a fingerprint-based identification of the user.

Figure 25:
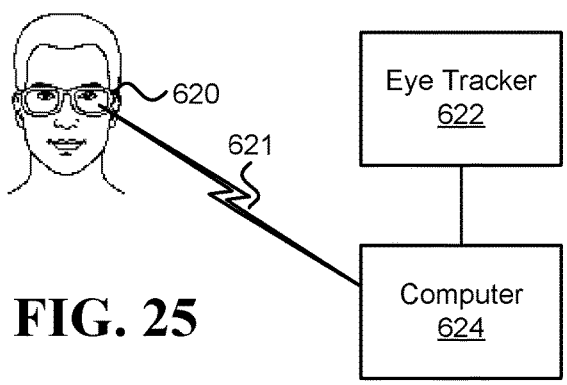
FIG. 25 is a schematic illustration of a system that includes a frame, CAM, a computer, and an eye tracker.

In one embodiment, a system that identifies whether a visual content (such as a video) includes an item that agitates a user includes an eye tracker, CAM, and a computer. The system may optionally include other components, such as a frame that is worn on the user's head (to which CAM, the eye tracker, and/or other components may be physically coupled). Additionally, the system may optionally include one or more additional CAMs and one or more sensors (which are not CAMs). The system may also include a head-mounted display (HMD) to display video to the user. FIG. 25 is a schematic illustration of such a system that includes frame 620 with CAM coupled to it, a computer 624, and an eye tracker 622.

CAM takes thermal measurements of an ROI ($TH_{ROI}$) on the user's face. Optionally, CAM is located less than 15 cm from the user's face. Optionally, CAM weighs less than 10 g. The ROI exhibits a change in temperature when the user experiences stress, such as the periorbital areas around the eyes, the nose, and/or the forehead.

In one embodiment, $TH_{ROI}$ are taken during a window of time that lasts between a second to a few minutes during which the user views a visual content that depicts items. Optionally, the window is at least five seconds long, at least thirty seconds long, at least two minutes long, at least five minutes long, at least fifteen minutes long, at least one hour long, or is some other window that is longer than one second. Optionally, during the time the user is exposed to the visual content, $TH_{ROI}$ from multiple windows may be evaluated (e.g., using a sliding window approach).

The eye tracker tracks the user's gaze while watching the video that depicts items. Optionally, the user's gaze is indicative of attention the user paid to the items. Optionally, data generated by the eye tracker is indicative of attention the user paid to each of the items. The eye tracker may be head-mounted or non-head-mounted.

The data generated by the eye tracker describes the gaze of the user. For example, the data may be indicative of the coordinates, on a display displaying the visual content (e.g., video), on which the user focused during various times while watching the video. Optionally, the coordinates represent certain pixels and/or sets of pixels. This information may be analyzed along with information that describes the boundaries (e.g., coordinates) of the items in the video at different times during its presentation in order to determine when the user focuses on each item. Optionally, determining which items were presented in the video may involve utilizing various image processing algorithms, which can identify items (e.g., objects and/or people) in the video and/or define the boundaries of the items in the video at various times. Thus, using the data generated by the eye tracker, attention levels of the user in at least some of the items can be determined (e.g., by the computer). In one example, an attention level of the user in an item is indicative of the amount of time the user spent focusing on the item (e.g., before moving to another item). In another example, the attention level of the user in an item is indicative of the number of times the user's sight was focused on the item during certain duration. In still another example, the attention level of the user is a relative value, which indicates whether the user paid more attention or less attention to the item compared to the other items in the video.

The computer is configured, in some embodiments, to detect, based on $TH_{ROI}$ taken while the user views the video, a stress level of the user. Additionally, the computer is configured to calculate an extent of discordance between the attention the user paid to the items and expected attention levels in the items. These two values (the stress level and extent of discordance) are utilized by the computer to determine whether at least one of the items agitated the user. In one embodiment, if the stress level reaches a first threshold and the extent of discordance reaches a second threshold, the computer makes a determination that at least one of the items in the video agitated the user. In another embodiment, the computer calculates, based on the stress level and the extent of discordance, a value indicative of a probability that the items include an item that agitates the user. Optionally, if the value indicates a probability above a third threshold, the computer makes a determination that at least one of the items in the video agitated the user.

The value indicative of the probability that the items include an item that agitates the user is, in some embodiments, proportional to a product of the stress level and the extent of the discordance. That is, in most scenarios, the larger one or both of these values (the stress level and the extent of the discordance), the larger probability that the items include an item that agitates the user. In one example, the value is indicative of negative feelings related to an item and/or a situation presented in the video (the larger the value the likelier it is that the user harbors such negative feelings). In another example, the value is indicative of an extent to which it is likely that the user is concealing something related to the content of the video.

In one embodiment, the computer may utilize the stress levels and the information of the user's gaze to select the item, from among the items depicted in the video, which agitates the user. Optionally, agitation due to the item may be manifested by an increase of at least a certain level in the stress of the user and/or by the user having an atypical gaze pattern in which the user pays significantly less attention or significantly more attention to the item than expected. In one example, "significantly more attention" refers to staring at the item at least double the expected time, and "significantly less attention" refers to staring at the item less than half the expected time.

The expected attention levels in the items may be based, in some embodiments, on tracking gazes during previous viewings of the video and/or previous viewings of similar videos in order to determine attention in the items. In one embodiment, the attention levels in the items are based on attention levels detected when the same video was viewed by other people. For example, the attention levels may represent the average attention paid by the other users to each item. In another embodiment, the attention levels in the items are based on attention levels of the user to items in similar videos. For example, if the video depicts a scene (e.g., a person filling out a loan application), then a similar video may include the same scene, possibly with slightly different items (e.g., a different person filling out a loan application).

In some embodiments, determining the expected attention levels in the items may involve utilizing a model. Optionally, the model is trained based on previous tracking of the user's gaze when observing other videos. Additionally or alternatively, the model is trained based on tracking of other users' gaze when observing other videos. Optionally, the model may be generated using one or more of the various attention modelling algorithms known in the art (such algorithms may also be referred to as saliency mapping algorithms). Some of the many algorithms that may be utilized are surveyed in A. Borji, L. Itti, "State-of-the-Art in Visual Attention Modeling", IEEE Transactions on Pattern Analysis & Machine Intelligence vol. 35(1), p. 185-207, 2013.

In one embodiment, a model for attention in visual items may be generated by creating a training set of samples. Where each sample corresponds to an item in a video and includes features values and a label describing the extent of attention in the item. Various feature values may be included in each sample. For example, some feature values may be generated using various image processing techniques and represent various low-level image properties. Some examples of such features may include features generated using Gabor filters, local binary patterns and their derivatives, features generated using algorithms such as SIFT, SURF, and/or ORB, and features generated using PCA or LDA. In another example, at least some feature values may include higher-level description of the items (e.g., after identification of the items and/or actions depicted in the video). In yet another example, some feature values may describe the user viewing the video (e.g., demographic information about the user and/or data related to the user's physiological state). A collection of samples, such as the ones described above, may be provided to a machine learning-based training algorithm in order to train the model. Some examples of the types of models that may be generated include support vector machines (SVMs) and neural networks.

Obtaining the expected attention levels may be done in various ways. In one embodiment, values of the attention levels are determined based on tracking the gaze of the user (and/or other users) in previous viewing the video and/or similar videos; the attention levels determined in this tracking may be used as the expected attention levels in the items displayed in the video while $TH_{ROI}$ are taken. In another embodiment, feature values are generated based on the video and/or a description of the user, and the expected attention values are calculated based on the feature values utilizing a model for attention in visual items, as described above.

In one embodiment, the expected attention levels comprise values of attention in two or more of the items. Additionally, the attention the user paid to the two or more items is determined based on the gaze of the user. These two sets of values may be compared in order to calculate the extent of the discordance between the attention the user paid to the items and expected attention levels in the items. In one example, a divergence metric, such as the Kullback-Leibler divergence may be used to calculate the discordance between the two sets of values. In another example, a distance metric, such as a vector dot product may be used to calculate the discordance between the two sets of values.

In another embodiment, the expected attention levels comprise an indication of a subset comprising one or more of the items to which the user is expected to pay at least a certain amount of attention or one or more of the items to which the user is expected to pay at most a certain amount of attention. Additionally, a subset of the items to which the user paid at least the certain amount of attention (or at most the certain amount of attention), is determined based on the gaze of the user. In this embodiment, a comparison between the subset of items selected based on expected attention levels and the subset selected based on the gaze of the user may be done in order to calculate the extent of the discordance between the attention the user paid to the items and expected attention levels in the items. In one example, the extent of the discordance is proportional to the size of the symmetric difference between the two subsets.

In one embodiment, the stress level is calculated by comparing one or more values derived from $TH_{ROI}$ to a certain threshold, and determining whether the threshold is reached (which is indicative of an occurrence of at least a certain amount of stress). Optionally, the certain threshold is determined based on previous thermal measurements of the user taken with CAM. Optionally, most of the previous measurements were taken while the user was not under elevated stress. Alternatively, most of the previous measurements were taken while the user was under elevated stress. Optionally, the certain threshold is determined based on baseline thermal measurements of the user, and the certain threshold represents a difference of a certain magnitude relative to the baseline measurements. Optionally, different thresholds may be utilized to detect the stress level when the user is in a certain emotional state and/or is in an environment characterized by certain environmental conditions.

In another embodiment, the stress level is calculated by generating feature values based on $TH_{ROI}$ and utilizing a machine learning-based model to calculate, based on the feature values, a stress level experienced by the user. Optionally, at least some of the feature values are generated based on the video, e.g., the at least some of the feature values describe properties of the items depicted in the video. In one example, the model is trained based on previous $TH_{ROI}$ taken while the user had at least two different stress levels according to a predetermined stress scale. In another example, the model is trained based on thermal measurements of other users (e.g., the model is a general model). Optionally, at least some of the feature values describe the emotional state of the user and/or environmental conditions corresponding to when $TH_{ROI}$ were taken. Optionally, at least some of the feature values are generated based on previous $TH_{ROI}$ taken before the user viewed the video (e.g., up to 15 minutes before); thus, when determining the extent of stress the user experienced, the computer can account for the user's baseline stress level.

In some embodiments, at least some feature values utilized to calculate the stress level may be based on thermal measurements obtained with other thermal cameras. In one embodiment, the ROI is on a periorbital area, and the system includes second and third CAMs configured to take thermal measurements of a region on the forehead ($TH_{ROI2}$) of the user and thermal measurements of a region on the nose ($TH_{ROI3}$) of the user, respectively. Optionally, the computer detects the stress level also based on $TH_{ROI1}$ and/or $TH_{ROI3}$. In one example, the computer generates feature values based on $TH_{ROI}$ and on $TH_{ROI1}$ and/or $TH_{ROI3}$, and utilizes a certain model to calculate, based on the feature values, the stress level of the user. In this example, the certain model is trained based on previous $TH_{ROI}$ and $TH_{ROI1}$ and/or $TH_{ROI3}$ taken while the user had at least two different stress levels according to a predetermined stress scale.

There are various ways in which the computer may calculate, based on the stress level and the extent of discordance, a value indicative of a probability that the items include an item that agitates the user.

In one embodiment, the value indicative of the probability is calculated by comparing the stress level and the extent of discordance to corresponding thresholds. For example, when the stress level reaches at least a certain level and the discordance is at least a certain extent, that is indicative that there is at least a certain probability that that the items include an item that agitates the user. Optionally, calculating the probability involves utilizing a table that includes probability values for different combinations of thresholds (i.e., for different combinations of minimal stress levels and extents of discordance). Optionally, the table is generated based on observations of events in which the extent of stress of users was measured along with the extent of discordance based on their gaze, along with indications of whether the events involved a video that includes an item that agitated the viewer.

In another embodiment, the computer generates feature values based on the stress level and the extent of discordance and utilizes a machine learning-based model to calculate, based on the feature values, the probability that the items include an item that agitates the user. It is to be noted that this machine learning-based model is a different model than the one used in the embodiment described further above to detect the stress level. Optionally, the feature values include at least some features values indicative of the value of the stress level and/or the extent of discordance. Optionally, the feature values include at least one feature value indicative of a difference between the stress level and a baseline stress level of the user. Optionally, the feature values include at least one feature value that describes the video. For example, the at least one feature values may be indicative of what types of items are presented in the video. Optionally, the feature values include at least one feature value describing the user (e.g., the at least one feature value may be indicative of values such as the user's, the user's gender, the user's occupation, etc.) Optionally, the machine learning-based model is trained based on samples generated from previous events in which the extent of stress of users was measured along with the extent of discordance based on their gaze, along with indications of whether the events involved a video that includes an item that agitated the viewer.

When utilizing feature values along with a machine learning-based model, such as the model used to detect the stress level or the model used to calculate the value indicative of the probability that the items in the video include an item that agitates the user, in some embodiments, the feature values may include values based on additional inputs. In one example, the computer (i) receives one or more values indicative of at least one of the following parameters of the user: heart rate, heart rate variability, galvanic skin response, respiratory rate, and respiratory rate variability, and (ii) generates one or more of the feature values based on the one or more values. In another example, the computer (i) receives one or more values measured by at least one of the following sensors coupled to the user: a photoplethysmogram (PPG) sensor, an electrocardiogram (ECG) sensor, an electroencephalography (EEG) sensor, a galvanic skin response (GSR) sensor, and a thermistor, and (ii) generates one or more of the feature values based on the one or more values. In yet another example, the computer (i) receives one or more values indicative of whether the user touched at least one of the eyes, whether the user is engaged in physical activity, and/or an environmental parameter, and (ii) generates one or more of the feature values based on the one or more values. In still another example, the computer (i) receives one or more values measured by an accelerometer, a pedometer, a humidity sensor, a miniature radar, a miniature active electro-optics distance measurement device, an anemometer, an acoustic sensor, and/or a light meter, and (ii) generates one or more of the feature values based on the one or more values. And in another example, the computer (i) receives values indicative of at least one of the following properties describing the user: age, gender, weight, height, health problems, mental health problems, occupation, education level, marital status, and (ii) generates one or more of the feature values based on the one or more values.

Figure 27:
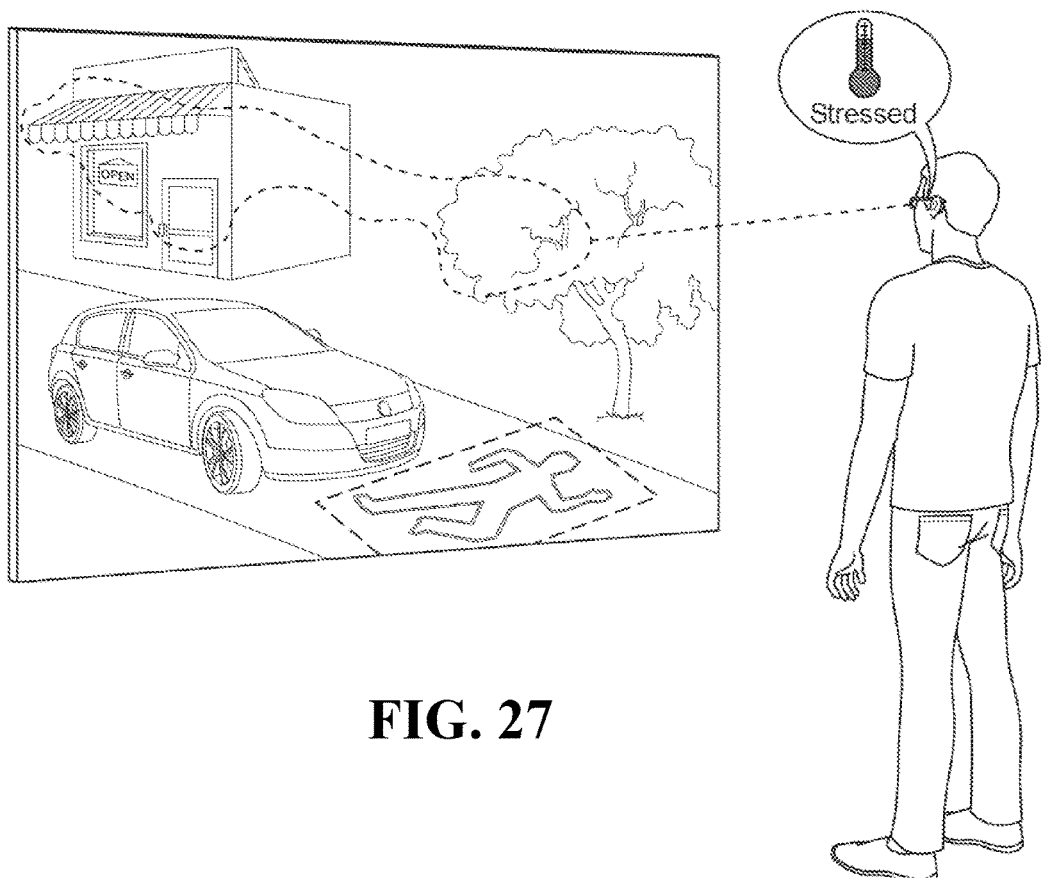
FIG. 27 illustrates a scenario that identifies that a user is agitated from viewing a video.

FIG. 27 illustrates a scenario in which an embodiment of a system described above is utilized to identify that a user is agitated (stressed) from viewing a video. In this scenario, a user is measured with CAMs coupled to a frame worn on the user's head while viewing an image of an accident scene. Eye tracking reveals that the user is avoiding a region that corresponds to the accident and the thermal measurements indicate an elevated stress level. Thus, the system may indicate that there is a high probability that the scene includes something that particularly agitates the user.

In one embodiment, a system configured to identify whether a visual content includes an item that agitates a user, includes: an eye tracker configured to track the user's gaze while watching a visual content depicting items; where the user's gaze is indicative of attention the user paid to the items; an inward-facing head-mounted thermal camera (CAM) configured to take thermal measurements of a region of interest on the face ($TH_{ROI}$) of the user; and a computer configured to: calculate stress levels based on $TH_{ROI}$, calculate an extent of discordance between the attention the user paid to the items and expected attention levels in the items, and determine, based on the stress level and the extent of discordance, whether at least one of the items agitated the user.

The following is a description of steps involved in one embodiment of a method for identifying when video includes an item that agitates a user. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method. In one embodiment, the method includes at least the following steps:

In Step 1, tracking the user's gaze while the user watches a video depicting items. Optionally, the user's gaze is indicative of attention the user paid to the items. Optionally, tracking the user's gaze is performed by an eye tracker.

In Step 2, taking thermal measurements of a region of interest on the face ($TH_{ROI}$) of the user, while the user watches the video, with an inward-facing head-mounted thermal camera.

In Step 3, calculating stress levels based on $TH_{ROI}$.

In Step 4, calculating an extent of discordance between the attention the user paid to the items and expected attention levels in the items.

And in Step 5, calculating, based on the stress level and the extent of discordance, a value indicative of a probability that the items include an item that agitates the user.

In one embodiment, the method may optionally include a step involving calculating the expected attention levels in the items utilizing a model of the user. Optionally, the model used in this step was trained based on previous tracking of the user's gaze when observing other videos. Additionally or alternatively, calculating the expected attention levels in the items using a saliency mapping algorithm.

In another embodiment, the method may optionally include a step involving calculating, based on $TH_{ROI}$, stress levels corresponding to different times, and utilizing tracking of the user's gaze to assign stress levels to different items.

In yet another embodiment, the method may optionally include a step involving identifying that an item from among the items is a suspicious item based on the stress level reaching a first threshold and a difference between the attention the user paid to the item and the expected attention to the item reaching a second threshold.

Some aspects of this disclosure involve monitoring a user while performing his or her job in order to create a model of the user's typical behavior. This monitoring may involve determining the typical stress levels of the user and gaze patterns (e.g., what the user typically pays attention too when performing the usual activities on the job). When the user exhibits atypical behavior while performing a job, it may be an indication that something illicit and/or illegal is being performed. For example, a bank loan officer knowingly approving a faulty loan may exhibit higher stress levels while evaluating the loan forms and may also have a significantly different gaze pattern compared to when working on a usual loan application. In another example, a doctor examining a patient in order to assist in a faulty insurance claim may also be more stressed and/or have a different gaze pattern. In yet another example, a customs official "looking the other way" when an accomplice smuggles contraband is also expected to have elevated stress levels and a different gaze pattern than ordinarily observed on the job. When atypical behavior is detected, it can be noted in order to have the event to which it corresponds inspected more thoroughly by other parties (e.g., a supervisor).

Figure 28A:
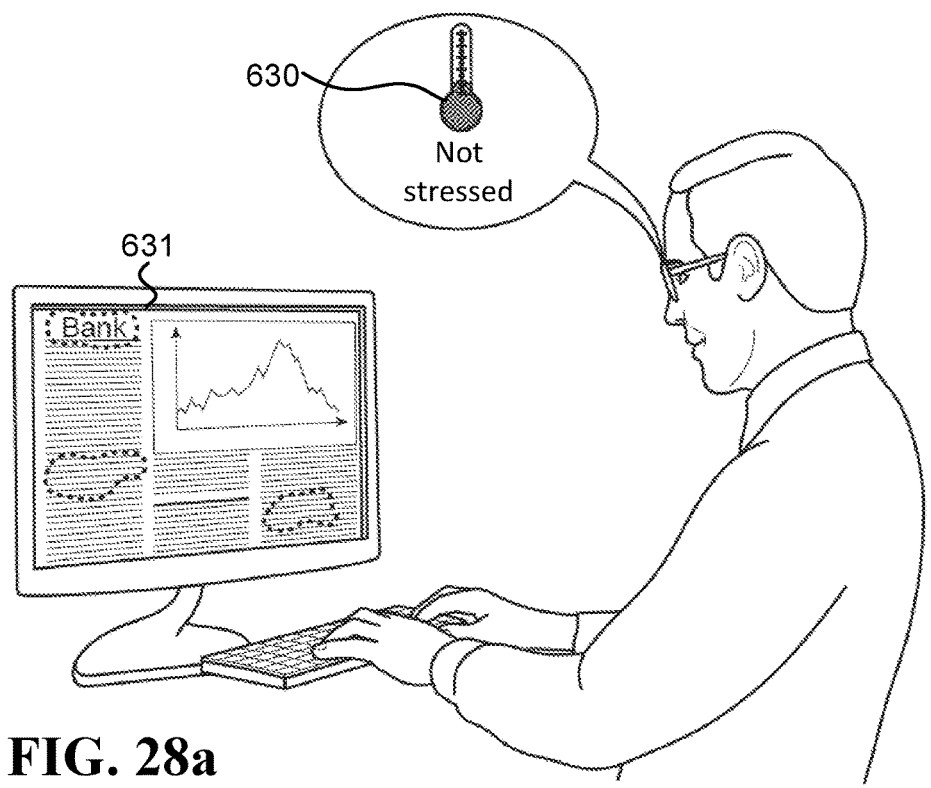
FIG. 28a and FIG. 28b illustrate scenarios in which stress levels and gaze patterns are utilized do detect atypical user behavior.
Figure 28B:
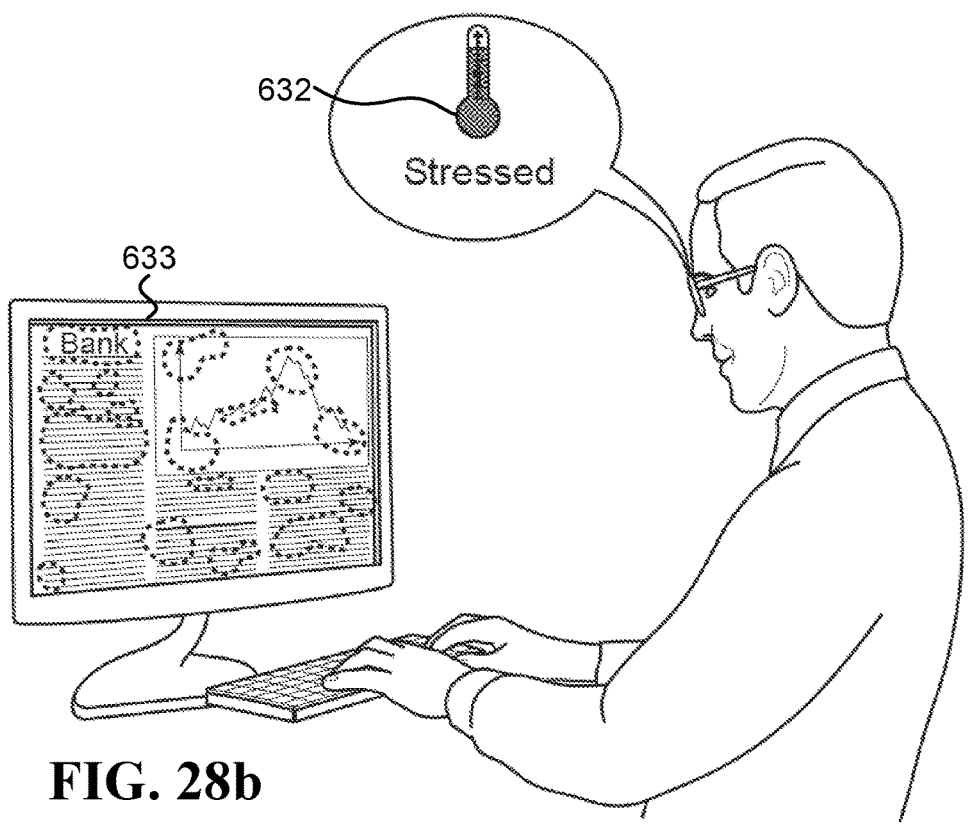

FIG. 28a and FIG. 28b illustrate a scenario in which stress levels and gaze patterns may be utilized do detect atypical user behavior. FIG. 28a illustrates a typical gaze pattern of the user shown as dashed-line closed-shapes on screen 631 (obtained using eye tracking), while the user performs his job at a computer terminal. Thermal measurements of the user 630 indicate that the user is not stressed. FIG. 28b illustrates an instance in which the user has an atypical gaze pattern shown as dashed-line closed-shapes on screen 633, and in addition, the thermal measurements of the user 632 indicate that the user is stressed. Embodiments of the system described below can identify the atypical gaze pattern and the user elevated stress level, and generate an indication that the user is behaving atypically.

In one embodiment, a system configured to identify atypical behavior of a user includes an eye tracker, a CAM, and a computer. CAM takes thermal measurements of a region of interest ($TH_{ROI}$) on the user's face. Optionally, CAM is located less than 15 cm from the face. Optionally, the ROI is on a periorbital area. Optionally, the system also includes a head-mounted display (HMD), which displays video to the user. The system may optionally include a frame which is worn on the user's head, and one or more of the following components are physically coupled to the frame: the HMD, CAM, the eye tracker, and the computer.

The eye tracker tracks the user's gaze while viewing items. Optionally, the user's gaze is indicative of attention of the user in the items. Optionally, the user's gaze is indicative of attention the user paid to each of the items. In one embodiment, the user's gaze is tracked while the user performs some work related task, such as performing office work (e.g., if the user is a clerk) or examining a patient (e.g., if the user is a doctor). Optionally, the user's gaze is tracked while the user views video related to the task the user is performing. In one example, the video is presented via the HMD, which may be a virtual reality display or an augmented reality display.

In some embodiments, the computer generates features values and utilizes a model to identify, based on the feature values, whether the user's behavior while viewing the items was atypical. Optionally, the feature values include feature values generated based on $TH_{ROI}$ taken while the user viewed the items and a set of feature values generated based on tracking the user's gaze. Optionally, the feature values generated based on the eye tracking are indicative of the attention of the user in the items. Optionally, the feature values may include at least some feature values indicative of expected attention levels in the items.

In one embodiment, the system configured to identify atypical behavior includes a second inward-facing head-mounted thermal camera that takes measurements of a second region on the face ($TH_{ROI2}$). Optionally, the computer generates one or more of the feature values used to detect the atypical behavior based on $TH_{ROI2}$. In one example, the second region is on the forehead. In another example, the second region is on the nose.

In another embodiment, the computer generates one or more of the feature values based on a difference between $TH_{ROI}$ and a baseline value determined based on a set of previous measurements taken by CAM. Optionally, most of the measurements belonging to the set were taken while the behavior of the user was not considered atypical according to the model.

In one embodiment, the model used to identify whether the user's behavior was atypical is generated based on previous tracking of the user's gaze while viewing other items and previous $TH_{ROI}$ taken during the viewing of the other items. Optionally, the user's behavior during most of the viewing of the other items was typical (i.e., it was not considered atypical). Optionally, the viewing of the previous items was done while the user was performing a similar activity to one performed by the user while $TH_{ROI}$ were taken. Optionally, the previous $TH_{ROI}$ were taken on different days. Optionally, the previous $TH_{ROI}$ were taken in different situations that include first $TH_{ROI}$ taken at most one hour before having a meal and second $TH_{ROI}$ taken at most one hour after having a meal. Optionally, the model is trained based on training samples, with each training sample corresponding to an event in which the user was monitored with the eye tracker and CAM, and each training sample comprising feature values generated based on a tracking of the user's gaze and $TH_{ROI}$ taken during the event.

In one embodiment, the model is indicative of a probability density function (pdf) of values derived from $TH_{ROI}$ and/or values derived from tracking the gaze of the user. For example, the model may be a regression model (e.g., a maximum entropy model) generated based on the training samples described above. Optionally, if the value calculated by the computer represents a probability that is below a threshold, the behavior of the user is considered atypical.

In another embodiment, the model describes one or more thresholds derived from $TH_{ROI}$ and/or values derived from tracking the gaze of the user. For example, the model may include typical ranges for $TH_{ROI}$, which are indicative of typical stress levels, and/or typical gaze patterns of the user, which are indicative of how much attention the user pays to different items. Optionally, if the user exhibits behavior that does not correspond to values in the ranges that appear in the model, that is indicative that the user's behavior while viewing the items was atypical.

The computer may calculate, based on $TH_{ROI}$ a value describing a stress level of the user. Additionally or alternatively, the computer may calculate an extent of discordance between the attention the user paid to the items and expected attention levels in the items. Optionally, the stress level and/or the extent of discordance are utilized by the computer to identify whether the user's behavior while viewing the items was atypical. For example, one or more of the feature values may be generated based on the stress level and/or one or more of the feature values may be generated based on the extent of the discordance.

In some embodiments, when the user's behavior while viewing the items was atypical, a stress level of the user during the viewing, which is calculated based on $TH_{ROI}$, reaches a threshold. The stress levels of the user during most of the time spent viewing the other items, as calculated based on the previous $TH_{ROI}$, do not reach the threshold. As discussed in more detail further above, there are various ways in which the computer may detect the stress level based on $TH_{ROI}$. In one embodiment, the stress level is calculated by comparing one or more values derived from $TH_{ROI}$ to a certain threshold, and determining whether the threshold is reached (which is indicative of an occurrence of at least a certain amount of stress). Optionally, the certain threshold is determined based on thermal measurements of the user (e.g., thermal measurements taken when the user was stressed). In another embodiment, the stress level is calculated by generating certain feature values based on $TH_{ROI}$ and utilizing a certain machine learning-based model to calculate, based on the certain feature values, the stress level experienced by the user.

In some embodiments, when the user's behavior while viewing the items was atypical, a divergence between the attention of the user in the items and expected attention of the user in the items is above a certain value. During most of the time spent viewing of the other items, divergences between the attention of the user in the other items and expected attention of the user in the other items were below the threshold. As discussed in more detail above, expected attention levels may be obtained in various ways. In one example, the expected attention levels in the other items are calculated utilizing a certain model of the user, which is trained based on previous tracking of the user's gaze. In another example, the expected attention levels in the other items are calculated utilizing a certain model that is trained based on tracking of other users' gaze. In yet another example, the expected attention levels in the other items are calculated using a saliency mapping algorithm.

When utilizing feature values along with a model, such as the certain model used to detect the stress level and/or the model used to identify whether the user's behavior was atypical, in some embodiments, the feature values may include values based on additional inputs (beyond $TH_{ROI}$), which are also utilized to detect the stress level. In one example, the computer (i) receives one or more values indicative of at least one of the following parameters of the user: heart rate, heart rate variability, galvanic skin response, respiratory rate, and respiratory rate variability, and (ii) generates one or more of the feature values based on the one or more values. In another example, the computer (i) receives one or more values measured by at least one of the following sensors coupled to the user: a photoplethysmogram (PPG) sensor, an electrocardiogram (ECG) sensor, an electroencephalography (EEG) sensor, a galvanic skin response (GSR) sensor, and a thermistor, and (ii) generates one or more of the feature values based on the one or more values. In yet another example, the computer (i) receives one or more values indicative of whether the user touched at least one of the eyes, whether the user is engaged in physical activity, and/or an environmental parameter, and (ii) generates one or more of the feature values based on the one or more values. In still another example, the computer (i) receives one or more values measured by an accelerometer, a pedometer, a humidity sensor, a miniature radar, a miniature active electro-optics distance measurement device, an anemometer, an acoustic sensor, and/or a light meter, and (ii) generates one or more of the feature values based on the one or more values. And in another example, the computer (i) receives values indicative of at least one of the following properties describing the user: age, gender, weight, height, health problems, mental health problems, occupation, education level, marital status, and (ii) generates one or more of the feature values based on the one or more values.

The following is a description of steps involved in one embodiment of a method for identifying atypical behavior. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method. In one embodiment, the method includes at least the following steps:

In Step 1, tracking the user's gaze while the user views items. Optionally, the user's gaze is indicative of attention the user paid to the items. Optionally, tracking the user's gaze is performed by the eye tracker described above.

In Step 2, taking thermal measurements of a region of interest ($TH_{ROI}$) on the user's face, while the user views the items, with an inward-facing head-mounted thermal camera.

In Step 3, generating feature values. Optionally, the generated feature values include feature values generated based on $TH_{ROI}$ and feature values based on the tracking in Step 1.

And in Step 4, utilizing a model to identify, based on the feature values generated in Step 3, whether the user's behavior, while viewing the items, was atypical. Optionally, the model was trained based on previous tracking of the user's gaze while viewing other items and previous $TH_{ROI}$ taken during the viewing of the other items.

In one embodiment, the method may optionally involve a step of calculating expected attention of the user in the items and generating at least some of the feature values based on the expected attention of the user in the items. Optionally, the user's gaze is indicative of attention of the user in the items, and when the user's behavior while viewing the items is atypical, a divergence between the attention of the user in the items and the expected attention of the user in the items is above a certain value.

In one embodiment, the method may optionally include steps that involve: taking, using a second inward-facing head-mounted thermal camera, additional thermal measurements of a region on the forehead, and generating one or more of the feature values used in Step 4, based on the additional thermal measurements.

In another embodiment, the method may optionally include steps that involve: taking, using a second inward-facing head-mounted thermal camera, additional thermal measurements of a region on the nose, and generating one or more of the feature values used in Step 4, based on the additional thermal measurements.

Normally, the lens plane and the sensor plane of a camera are parallel, and the plane of focus (PoF) is parallel to the lens and sensor planes. If a planar object is also parallel to the sensor plane, it can coincide with the PoF, and the entire object can be captured sharply. If the lens plane is tilted (not parallel) relative to the sensor plane, it will be in focus along a line where it intersects the PoF. The Scheimpflug principle is a known geometric rule that describes the orientation of the plane of focus of a camera when the lens plane is tilted relative to the sensor plane.

Figure 14A:
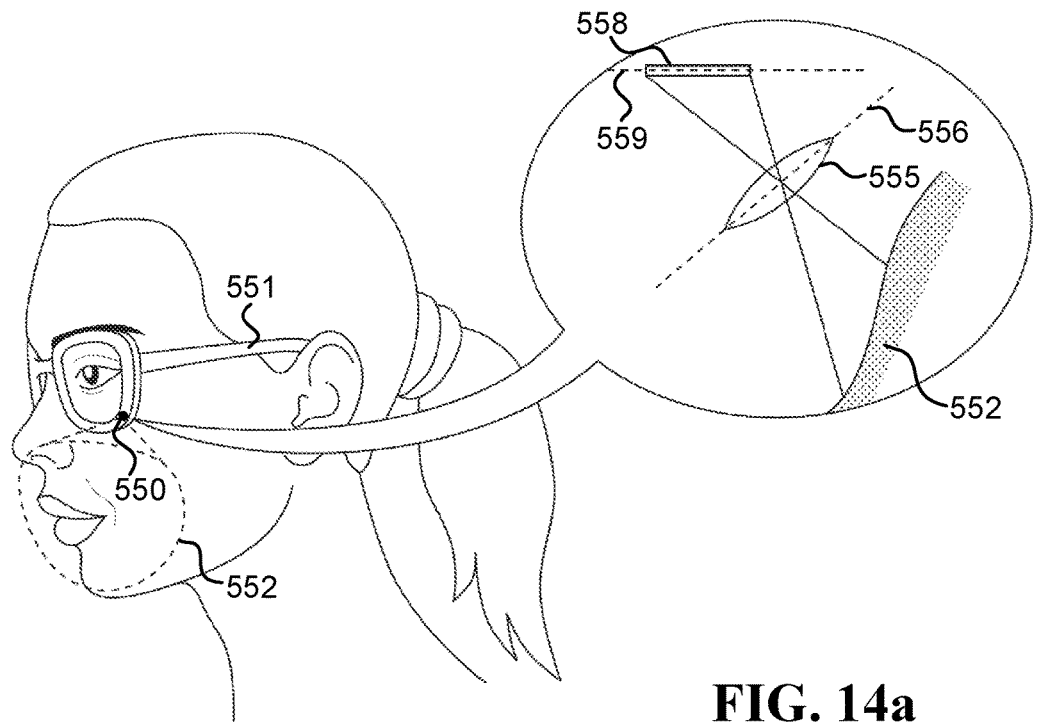
FIG. 14a is a schematic illustration of an inward-facing head-mounted camera embedded in an eyeglasses frame, which utilizes the Scheimpflug principle.

FIG. 14a is a schematic illustration of an inward-facing head-mounted camera 550 embedded in an eyeglasses frame 551, which utilizes the Scheimpflug principle to improve the sharpness of the image taken by the camera 550. The camera 550 includes a sensor 558 and a lens 555. The tilt of the lens 555 relative to sensor 558, which may also be considered as the angle between the lens plane 555 and the sensor plane 559, is determined according to the expected position of the camera 550 relative to the ROI 552 when the user wears the eyeglasses. For a refractive optical lens, the "lens plane" 556 refers to a plane that is perpendicular to the optical axis of the lens 555. Herein, the singular also includes the plural, and the term "lens" refers to one or more lenses. When "lens" refers to multiple lenses (which is usually the case in most modern cameras having a lens module with multiple lenses), then the "lens plane" refers to a plane that is perpendicular to the optical axis of the lens module.

Figure 14B:
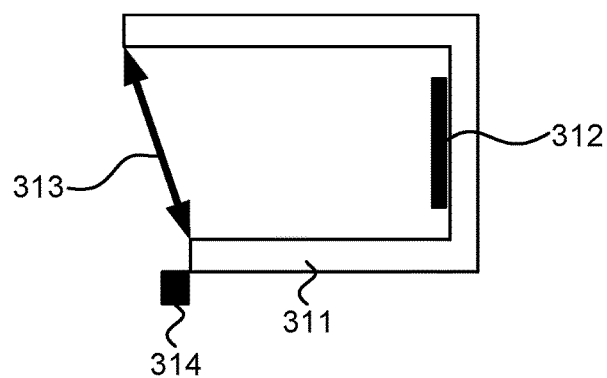
FIG. 14b is a schematic illustration of a camera that is able to change the relative tilt between its lens and sensor planes according to the Scheimpflug principle.

The Scheimpflug principle may be used for both thermal cameras (based on lenses and sensors for wavelengths longer than 2500 nm) and visible-light and/or near-IR cameras (based on lenses and sensors for wavelengths between 400-900 nm). FIG. 14b is a schematic illustration of a camera that is able to change the relative tilt between its lens and sensor planes according to the Scheimpflug principle. Housing 311 mounts a sensor 312 and lens 313. The lens 313 is tilted relative to the sensor 312. The tilt may be fixed according to the expected position of the camera relative to the ROI when the user wears the HMS, or may be adjusted using motor 314. The motor 314 may move the lens 313 and/or the sensor 312.

In one embodiment, the tilt between the lens plane and sensor plane is fixed. The fixed tilt is selected according to an expected orientation between the camera and the ROI when a user wears the frame. Having a fixed tilt between the lens and sensor planes may eliminate the need for an adjustable electromechanical tilting mechanism. As a result, a fixed tilt may reduce the weight and cost of the camera, while still providing a sharper image than an image that would be obtained from a similar camera in which the lens and sensor planes are parallel. The magnitude of the fixed tilt may be selected according to facial dimensions of an average user expected to wear the system, or according to a model of the specific user expected to wear the system in order to obtain the sharpest image.

Various embodiments described herein involve an HMS that may be connected, using wires and/or wirelessly, with a device carried by the user and/or a non-wearable device. The HMS may include a battery, a computer, sensors, and a transceiver.

Figure 29A:
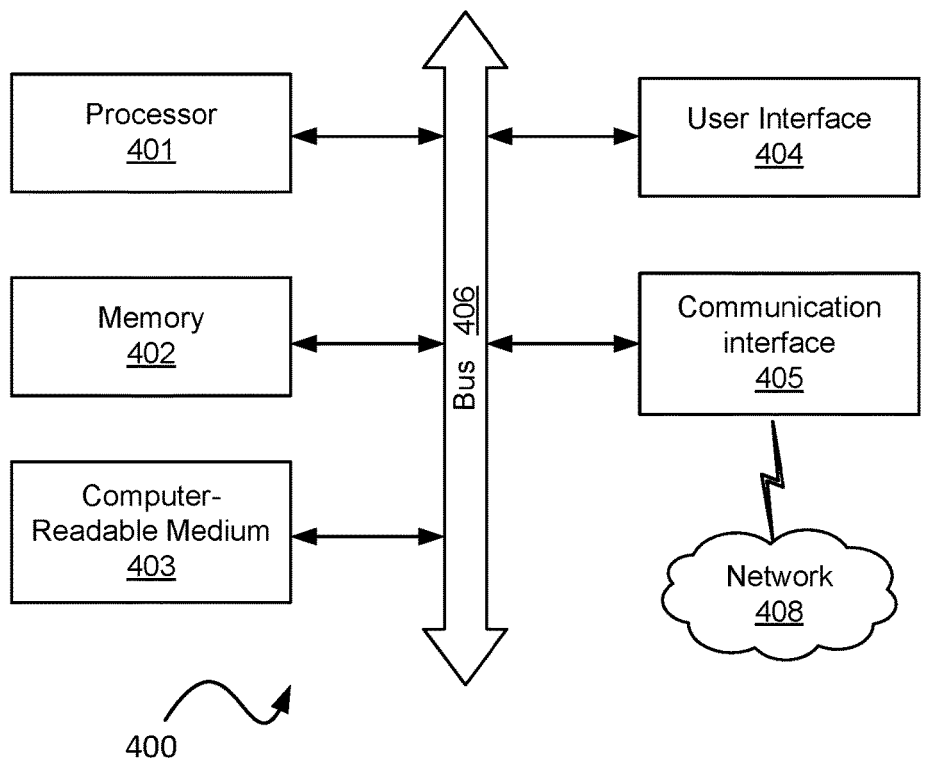
FIG. 29a and FIG. 29b are schematic illustrations of possible embodiments for computers.
Figure 29B:
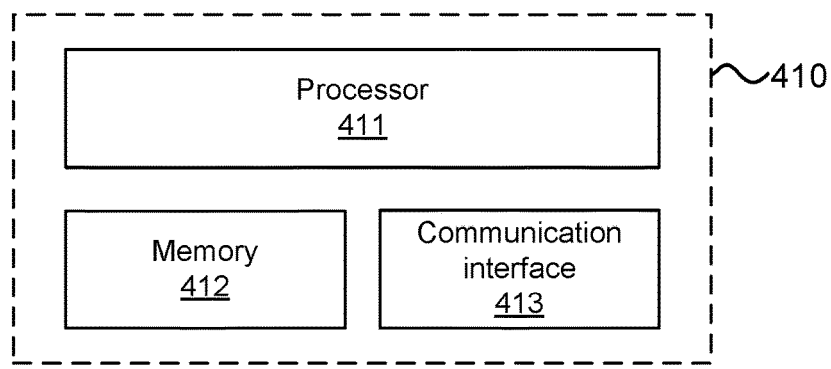

FIG. 29a and FIG. 29b are schematic illustrations of possible embodiments for computers (400, 410) that are able to realize one or more of the embodiments discussed herein that include a "computer". The computer (400, 410) may be implemented in various ways, such as, but not limited to, a server, a client, a personal computer, a network device, a handheld device (e.g., a smartphone), an HMS (such as smart glasses, an augmented reality system, and/or a virtual reality system), a computing device embedded in a wearable device (e.g., a smartwatch or a computer embedded in clothing), a computing device implanted in the human body, and/or any other computer form capable of executing a set of computer instructions. Herein, an augmented reality system refers also to a mixed reality system. Further, references to a computer or processor include any collection of one or more computers and/or processors (which may be at different locations) that individually or jointly execute one or more sets of computer instructions. For example, a first computer may be embedded in the HMS that communicates with a second computer embedded in the user's smartphone that communicates over the Internet with a cloud computer.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Thermal measurements that are forwarded to a processor/computer may include "raw" values that are essentially the same as the values measured by thermal cameras, and/or processed values that are the result of applying some form of preprocessing and/or analysis to the raw values. Examples of methods that may be used to process the raw values include analog signal processing, digital signal processing, and various forms of normalization, noise cancellation, and/or feature extraction.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non-transitory computer-readable medium.

Herein, a direction of the optical axis of a VCAM or a CAM that has focusing optics is determined by the focusing optics, while the direction of the optical axis of a CAM without focusing optics (such as a single pixel thermopile) is determined by the angle of maximum responsivity of its sensor. When optics are utilized to take measurements with a CAM, then the term CAM includes the optics (e.g., one or more lenses). In some embodiments, the optics of a CAM may include one or more lenses made of a material suitable for the required wavelength, such as one or more of the following materials: Calcium Fluoride, Gallium Arsenide, Germanium, Potassium Bromide, Sapphire, Silicon, Sodium Chloride, and Zinc Sulfide. In other embodiments, the CAM optics may include one or more diffractive optical elements, and/or or a combination of one or more diffractive optical elements and one or more refractive optical elements.

When CAM includes an optical limiter/field limiter/FOV limiter (such as a thermopile sensor inside a standard TO-39 package with a window, or a thermopile sensor with a polished metal field limiter), then the term CAM may also refer to the optical limiter. Depending on the context, the term CAM may also refer to a readout circuit adjacent to CAM, and/or to the housing that holds CAM.

Herein, references to thermal measurements in the context of calculating values based on thermal measurements, generating feature values based on thermal measurements, or comparison of thermal measurements, relate to the values of the thermal measurements (which are values of temperature or values of temperature changes). Thus, a sentence in the form of "calculating based on $TH_{ROI}$" may be interpreted as "calculating based on the values of $TH_{ROI}$", and a sentence in the form of "comparing $TH_{ROI1}$ and $TH_{ROI2}$" may be interpreted as "comparing values of $TH_{ROI1}$ and values of $TH_{ROI2}$".

Depending on the embodiment, thermal measurements of an ROI (usually denoted $TH_{ROI}$ or using a similar notation) may have various forms, such as time series, measurements taken according to a varying sampling frequency, and/or measurements taken at irregular intervals. In some embodiments, thermal measurements may include various statistics of the temperature measurements (T) and/or the changes to temperature measurements ($\Delta T$), such as minimum, maximum, and/or average values. Thermal measurements may be raw and/or processed values. When a thermal camera has multiple sensing elements (pixels), the thermal measurements may include values corresponding to each of the pixels, and/or include values representing processing of the values of the pixels. The thermal measurements may be normalized, such as normalized with respect to a baseline (which is based on earlier thermal measurements), time of day, day in the month, type of activity being conducted by the user, and/or various environmental parameters (e.g., the environment's temperature, humidity, radiation level, etc.).

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. For example, sentences in the form of "thermal measurements indicative of a physiological response" mean that the thermal measurements include information from which it is possible to infer the physiological response. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). Both a "portion" of something and a "region" of something refer herein to a value between a fraction of the something and 100% of the something. For example, sentences in the form of a "portion of an area" may cover between 0.1% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

Sentences in the form of "angle greater than 20°" refer to absolute values (which may be +20° or −20° in this example), unless specifically indicated, such as in a phrase having the form of "the optical axis of CAM is 20° above/below the Frankfort horizontal plane" where it is clearly indicated that the CAM is pointed upwards/downwards. The Frankfort horizontal plane is created by two lines from the superior aspects of the right/left external auditory canal to the most inferior point of the right/left orbital rims.

The terms "comprises," "comprising," "includes," "including," "has," "having", or any other variation thereof, indicate an open-ended claim language that does not exclude additional limitations. The "a" or "an" is employed to describe one or more, and the singular also includes the plural unless it is obvious that it is meant otherwise; for example, sentences in the form of "a CAM configured to take thermal measurements of a region ($TH_{ROI}$)" refers to one or more CAMs that take thermal measurements of one or more regions, including one CAM that takes thermal measurements of multiple regions; as another example, "a computer" refers to one or more computers, such as a combination of a wearable computer that operates together with a cloud computer.

The phrase "based on" is intended to mean "based, at least in part, on". Additionally, stating that a value is calculated "based on X" and following that, in a certain embodiment, that the value is calculated "also based on Y", means that in the certain embodiment, the value is calculated based on X and Y.

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to detect an irregular physiological response while being exposed to sensitive data, comprising:
   a head-mounted display (HMD) configured to expose sensitive data to a user who wears the HMD;
   an inward-facing head-mounted thermal camera (CAM) configured to take thermal measurements of a region of interest ($TH_{ROI}$) on the user's face while the user is exposed to the sensitive data; wherein CAM is located less than 15 cm from the face; and
   a computer configured to detect, based on certain $TH_{ROI}$ taken while the user was exposed to certain sensitive data, whether the user experienced the irregular physiological response while being exposed to the certain sensitive data.

2. The system of claim 1, wherein the certain sensitive data is associated with a first type of sensitive data, and the computer is configured to detect the irregular physiological response when a difference between the certain $TH_{ROI}$ and a first baseline reaches a first threshold; wherein the first baseline is calculated based on other $TH_{ROI}$ taken while the user was exposed to sensitive data associated with the first type of sensitive data; and further comprising a second certain sensitive data associated with a second type of sensitive data; and wherein the computer is further configured to detect the irregular physiological response when a difference between second certain $TH_{ROI}$ and a second baseline reaches a second threshold; wherein the second certain $TH_{ROI}$ are taken while the user is exposed to the second certain sensitive data, the second baseline is calculated based on other $TH_{ROI}$ taken while the user was exposed to sensitive data associated with the second type of sensitive data, and the second threshold is different from the first threshold.

3. The system of claim 2, wherein the system is further configured to estimate job burnout based on differences between $TH_{ROI}$ and their associated baselines; whereby the greater the differences between $TH_{ROI}$ and their associated baselines, the worse is the job burnout.

4. The system of claim 1, wherein the certain sensitive data is associated with a first type of sensitive data, and the computer is configured to detect the irregular physiological response when the certain $TH_{ROI}$ reach a first threshold; wherein the first threshold is calculated based on other $TH_{ROI}$ taken while the user was exposed to sensitive data associated with the first type of sensitive data; and further comprising a second certain sensitive data that is associated with a second type of sensitive data; and wherein the computer is further configured to detect the irregular physiological response when second certain $TH_{ROI}$ reach a second threshold; wherein the second certain $TH_{ROI}$ are taken while the user is exposed to the second certain sensitive data, the second threshold is calculated based on other $TH_{ROI}$ taken while the user was exposed to sensitive data associated with the second type of sensitive data, and the second threshold is different from the first threshold.

5. The system of claim 1, wherein the sensitive data is associated with a type of sensitive data belonging to a set comprising first and second types of sensitive data; wherein the computer is further configured to utilize $TH_{ROI}$ to generate feature values, and to utilize a machine learning-based model to calculate, based on the feature values, an extent of the irregular physiological response; and wherein the machine learning-based model was trained based on previous $TH_{ROI}$ of one or more users, taken during different days, and indications of which type of sensitive data the one or more users were exposed to; and wherein the previous $TH_{ROI}$ comprise at least some measurements taken while the one or more users were exposed to the first type of sensitive data and at least some measurements taken while the one or more users were exposed to the second type of sensitive data.

6. The system of claim 1, wherein the computer is further configured to receive values indicative of the user's emotional state while being exposed to the certain sensitive data, and to utilize a machine learning-based model to detect whether the user experienced the irregular physiological response based on the certain $TH_{ROI}$; wherein the machine learning-based model was trained based on previous $TH_{ROI}$ taken while the user was in a similar emotional state.

7. The system of claim 1, wherein the computer is further configured to receive values indicative of the environment the user was in while being exposed to the certain sensitive data, and to utilize a machine learning-based model to detect whether the user experienced the irregular physiological response based on the certain $TH_{ROI}$; wherein the machine learning-based model was trained based on previous $TH_{ROI}$ taken while the user was in a similar environment.

8. The system of claim 1, further comprising a sensor configured to provide measurements indicative of whether the user moved the HMD relative to the face while being exposed to the certain sensitive data; and, in response to detecting such movement, the computer is further configured to perform at least one of the following: (i) store in a database an indication that the user moved the HMD relative to the face while being exposed to the certain sensitive data, and (ii) restrict the user's ability to perform a certain transaction related to the certain sensitive data.

9. The system of claim 1, further comprising a sensor configured to provide measurements indicative of whether the user touches the region of interest (ROI), whereby touching the ROI is expected to affect $TH_{ROI}$; and, in response to detecting such a touch, the computer is further configured to store in a database an indication that the user touched the ROI while being exposed to the certain sensitive data.

10. The system of claim 9, wherein the computer is further configured to tighten security restrictions for the user responsive to detecting multiple occurrences where the user touched the ROI while being exposed to sensitive data that is of the same type as the certain sensitive data.

11. The system of claim 1, wherein CAM weighs below 10 g, and the system is further configured to detect occlusion of CAM based on performing at least one of the following: identifying a sudden change of more than 2° C. in $TH_{ROI}$, and utilizing a sensor configured to generate a signal indicative of whether a solid object is located between CAM and the region of interest (ROI); and, in response to detecting the occlusion, the computer is further configured to store in a database an indication that the user occluded CAM while being exposed to the certain sensitive data.

12. The system of claim 1, wherein the system receives the certain sensitive data in an encrypted form, and the computer is further configured to decrypt the certain sensitive data in order to expose the user to the certain sensitive data in an understandable form via the HMD; and further comprising a biometric identification device, physically coupled to the HMD, configured to identify the user while the user wears the HMD; wherein the computer is further configured to expose the user to the sensitive data responsive to receiving an indication that confirms the user's identity.

13. The system of claim 1, wherein the region of interest (ROI) is on a periorbital area of the user's face, and CAM comprises an uncooled thermal sensor.

14. The system of claim 1, wherein the ROI is on the periorbital area of the right eye; and further comprising a second inward-facing head-mounted thermal camera configured to take thermal measurements of a region on the periorbital area of the left eye ($TH_{ROI2}$); and wherein the computer is configured to detect the irregular physiological response based on both $TH_{ROI}$ and $TH_{ROI2}$.

15. The system of claim 1, wherein the ROI is on the user's nose and CAM comprises an uncooled thermal sensor.

16. The system of claim 1, wherein the ROI is on the right side of the user's nose; and further comprising a second inward-facing head-mounted thermal camera configured to take thermal measurements of a region on the left side of the nose ($TH_{ROI2}$); and wherein the computer is configured to detect the irregular physiological response based on both $TH_{ROI}$ and $TH_{ROI2}$.

17. The system of claim 1, wherein the ROI is on the user's forehead and CAM comprises an uncooled thermal sensor.

18. The system of claim 1, wherein the ROI is on the right side of the forehead; and further comprising a second inward-facing head-mounted thermal camera configured to take thermal measurements of a region on the left side of the forehead ($TH_{ROI2}$); and wherein the computer is configured to detect the irregular physiological response based on both $TH_{ROI}$ and $TH_{ROI2}$.

19. The system of claim 1, wherein the system is further configured to initiate a process to detect an illegal activity responsive to a detection of the irregular physiological response.

20. The system of claim 19, wherein the process is initiated within less than two minutes after detecting the irregular physiological response, the sensitive data belongs to an organization, the user is an employee of the organization, and the system helps in preventing illegal activities of employees related to sensitive data.

* * * * *